(12) United States Patent
Taguchi

(10) Patent No.: US 6,466,640 B1
(45) Date of Patent: Oct. 15, 2002

(54) COMPUTED TOMOGRAPHY SYSTEM AND METHOD

(75) Inventor: Katsuyuki Taguchi, Salt Lake City (JP)

(73) Assignee: Kabushiki Kaisha Toshiba, Tokyo (JP)

( * ) Notice: Subject to any disclaimer, the term of this patent is extended or adjusted under 35 U.S.C. 154(b) by 0 days.

(21) Appl. No.: 09/450,121

(22) Filed: Nov. 26, 1999

(51) Int. Cl.$^7$ ................................................. A61B 6/03
(52) U.S. Cl. ............................. 378/15; 378/4; 378/901
(58) Field of Search ........................... 378/4, 8, 15, 19, 378/901

(56) References Cited

U.S. PATENT DOCUMENTS

| | | | | |
|---|---|---|---|---|
| 5,271,055 A | * | 12/1993 | Hsieh et al. | 378/95 |
| 5,708,691 A | * | 1/1998 | Zmora | 378/4 |
| 5,825,842 A | | 10/1998 | Taguchi | 378/15 |
| 5,828,718 A | * | 10/1998 | Ruth et al. | 378/19 |
| 5,848,117 A | * | 12/1998 | Urchuk et al. | 378/19 |
| 5,966,422 A | * | 10/1999 | Dafni et al. | 378/9 |
| 5,974,108 A | * | 10/1999 | Taguchi et al. | 378/4 |
| 6,185,275 B1 | * | 2/2000 | Toth et al. | 378/113 |
| 6,072,851 A | * | 6/2000 | Sivers | 378/15 |
| 6,118,839 A | * | 9/2000 | Dafni et al. | 378/15 |
| 6,154,516 A | * | 11/2000 | Heuscher et al. | 378/15 |
| 6,275,560 B1 | * | 8/2001 | Blake et al. | 378/8 |

FOREIGN PATENT DOCUMENTS

| | | |
|---|---|---|
| JP | 9-234195 | 9/1997 |
| JP | 10-24031 | 1/1998 |
| JP | 10-286253 | 10/1998 |

OTHER PUBLICATIONS

K. Taguchi, et al., Med. Phys., vol. 25, No. 4, pps. 550–561, "Algorithm For Image Reconstruction in Multi–Slice Helical CT", Apr. 1998.

K. Taguchi, et al., Jpn. J. Radiol. Technol., vol. 55, No. 2, pps. 155–164, "Multi–Slice CT", Feb. 1999.

H. Bruder, et al., Part of the SPIE Conference on Image Processing, SPIE vol. 3661, pps. 420–432, "High Temporal Resolution vol. Heart Imaging with Multirow Computed Tomography", Feb. 1999.

H. Hu, et al., Proceedings of the 1999 International Meeting on Fully Three–Dimensional Image Reconstruction in Radiology and Nuclear Medicine, pps. 319–322, "Multi–Slice Helical CT: Scan and Image Temporal Resolution", Jun. 22, 1999.

F. Noo, et al., Phys. Med. Biol., vol. 44, pps. 561–570, "Single–Slice Rebinning Method for Helical Cone–Beam CT", 1999.

C.R. Crawford, et al., Med. Phys., vol. 17, No. 6, pps. 967–982, "Computed Tomography Scanning with Simultaneous Patient Translation", Nov./Dec., 1990.

\* cited by examiner

Primary Examiner—David V. Bruce
(74) Attorney, Agent, or Firm—Oblon, Spivak, McClelland, Maier & Neustadt, P.C.

(57) ABSTRACT

Method and system for computed tomography. Data is collected by irradiating a subject with x-rays. The data is interpolated and then weighted based upon the data collection time. The interpolated and weighted data is then used to reconstruct the image using fan beam reconstruction. The weighting function may by shifted in time. Signals may be obtained from the subject and used to control exposure, reduce the dose and provide automatic volumetric cardiac reconstruction. The method and system can increase the temporal and spatial resolution, and reconstruct images at different timing.

43 Claims, 26 Drawing Sheets

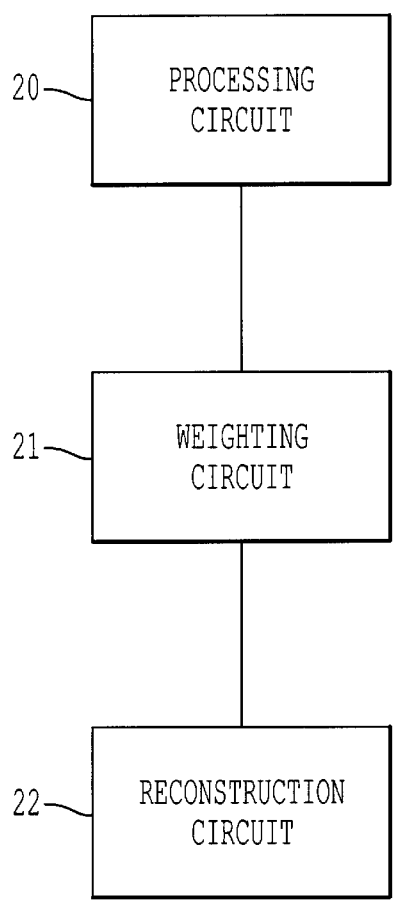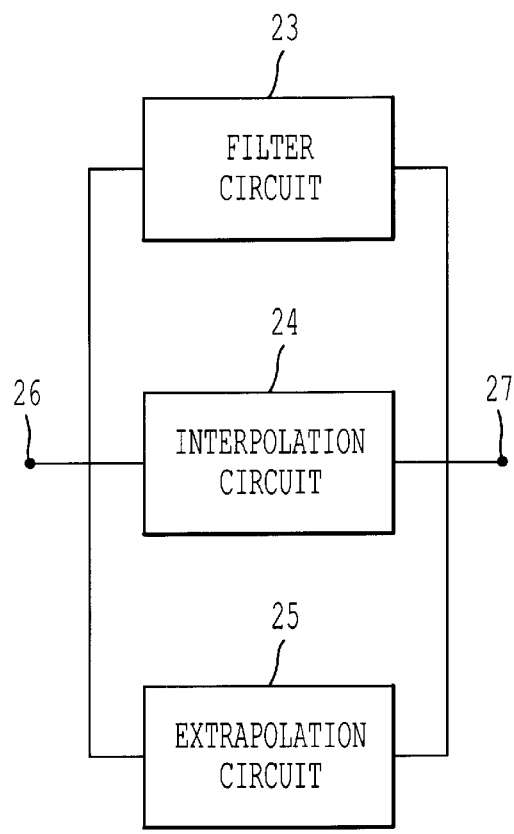

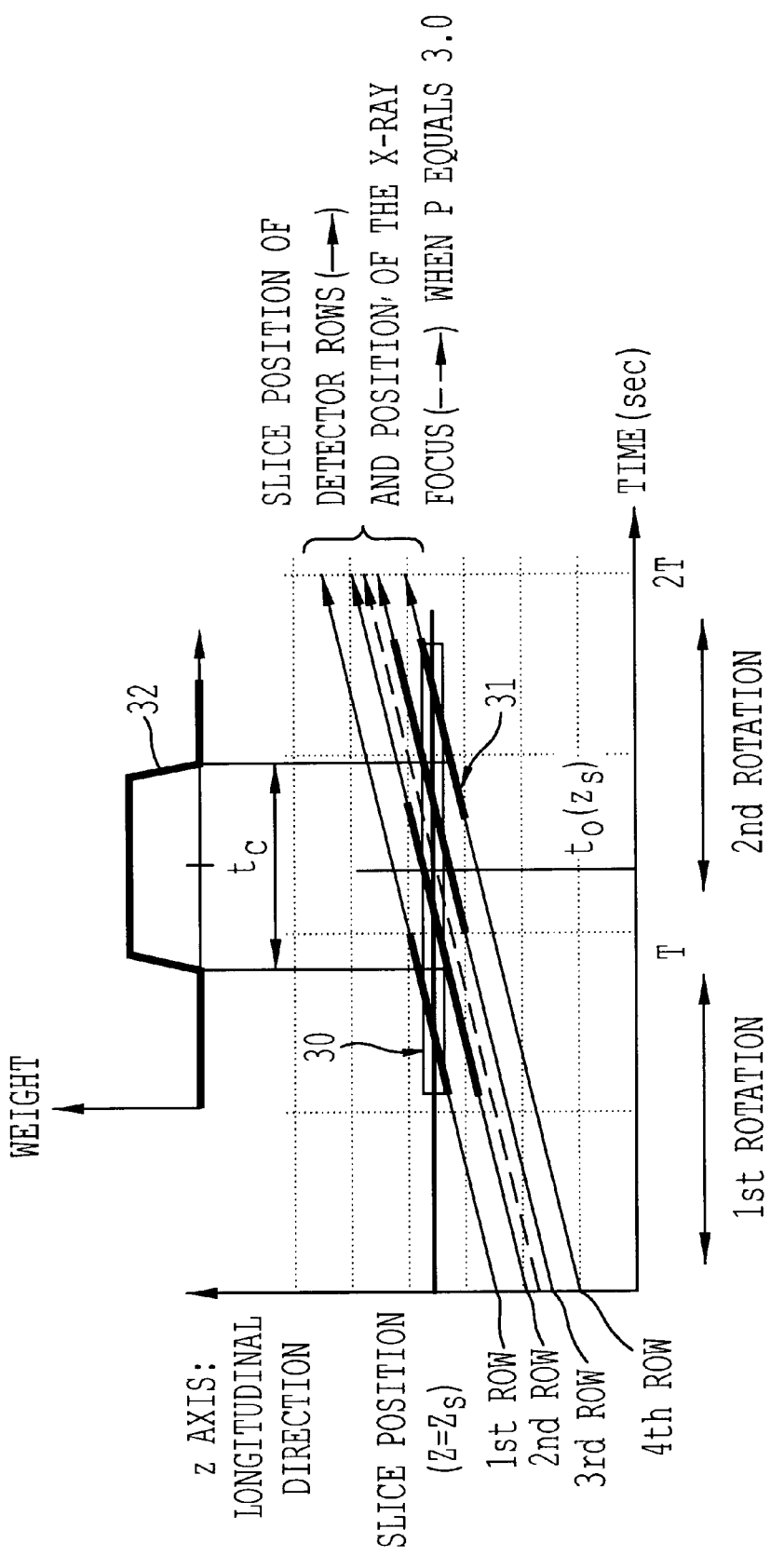

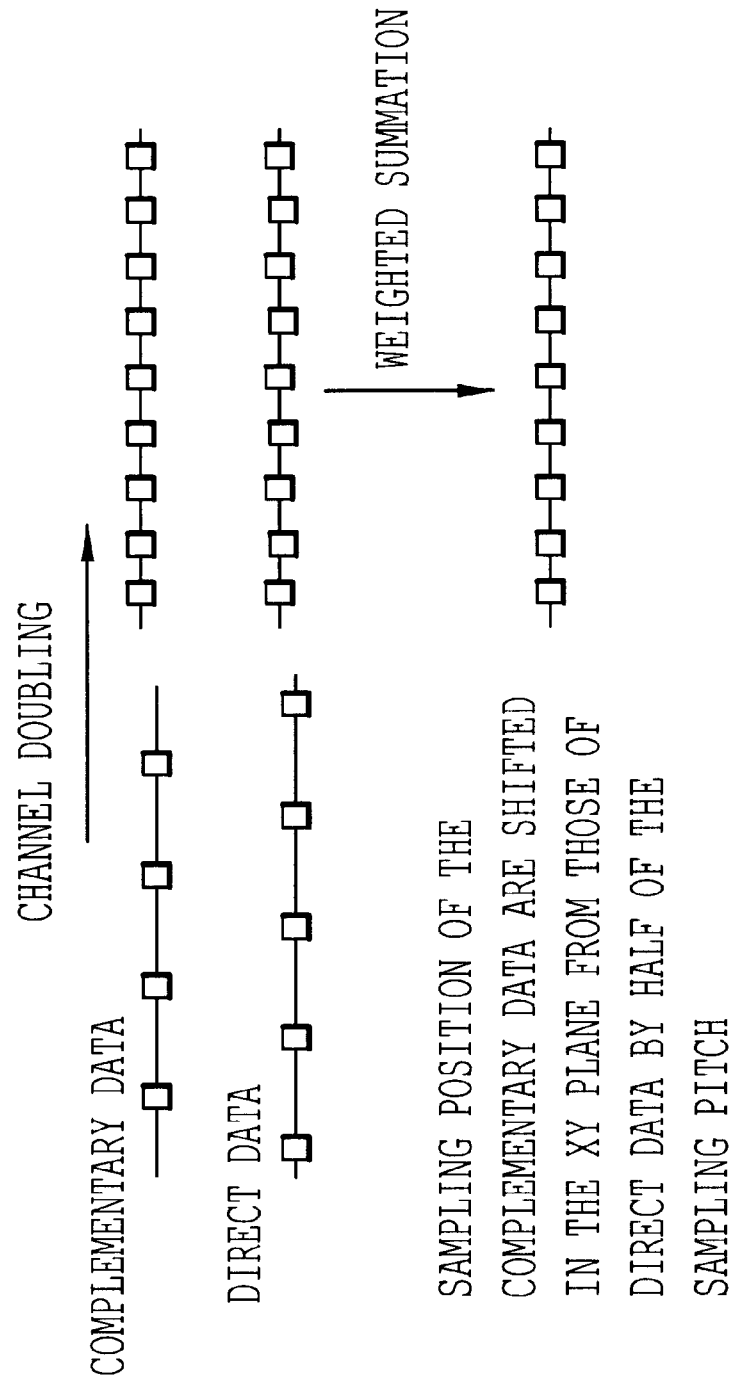

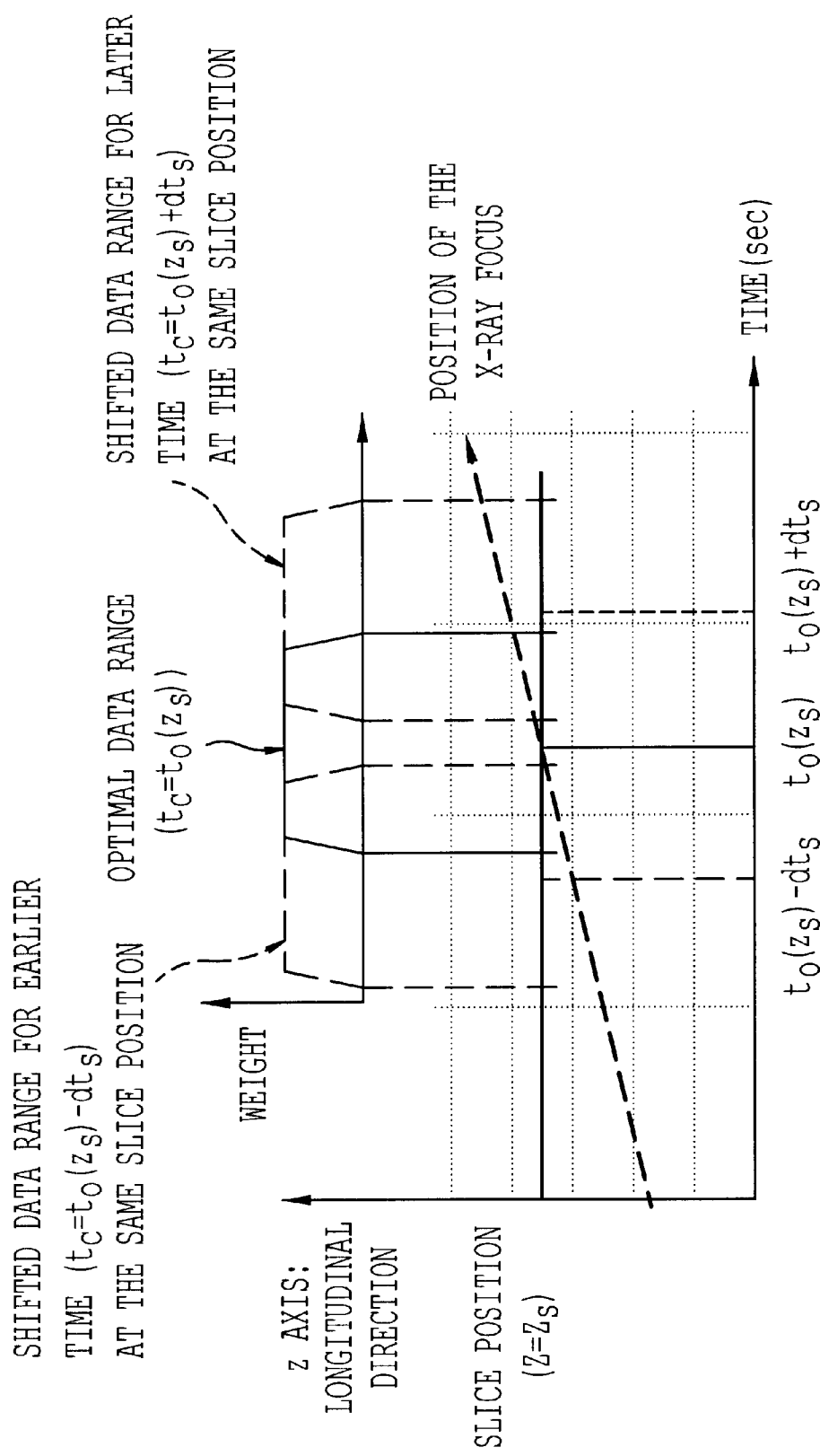

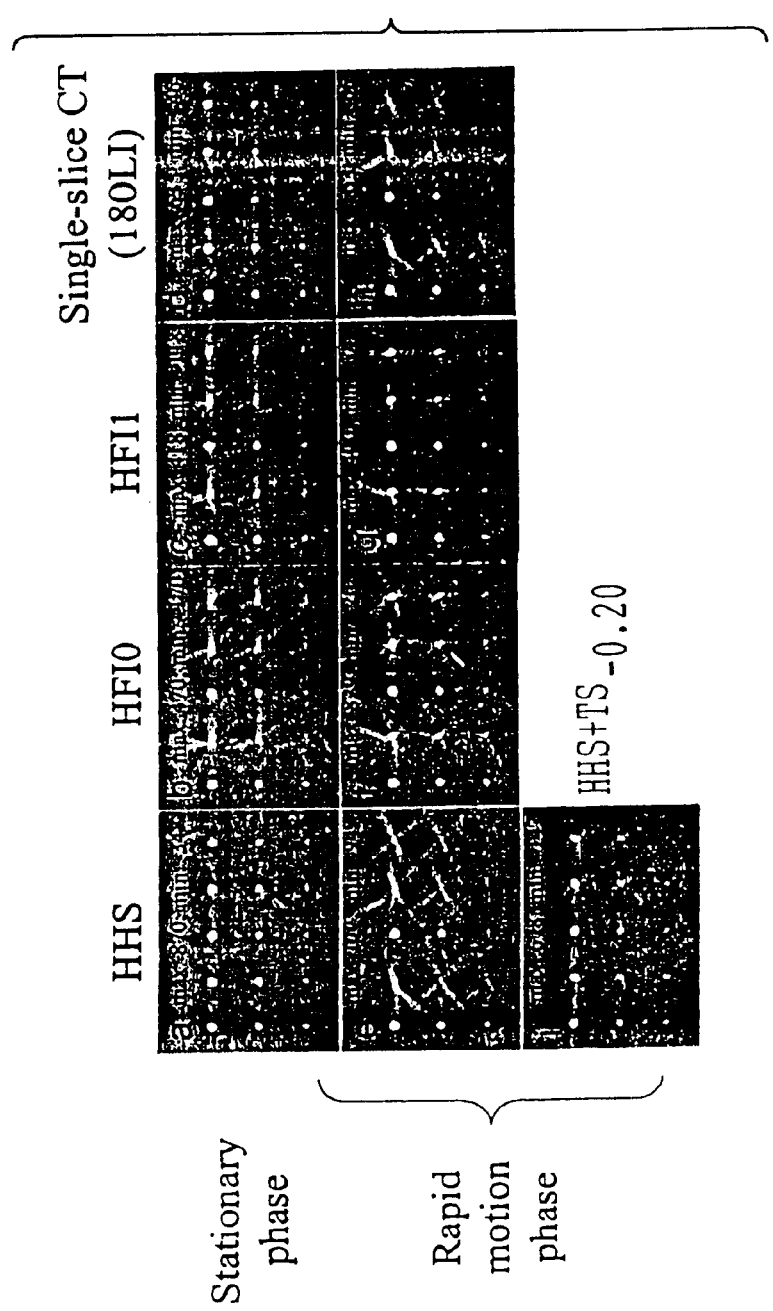

HFI0

HFI1

HHS1

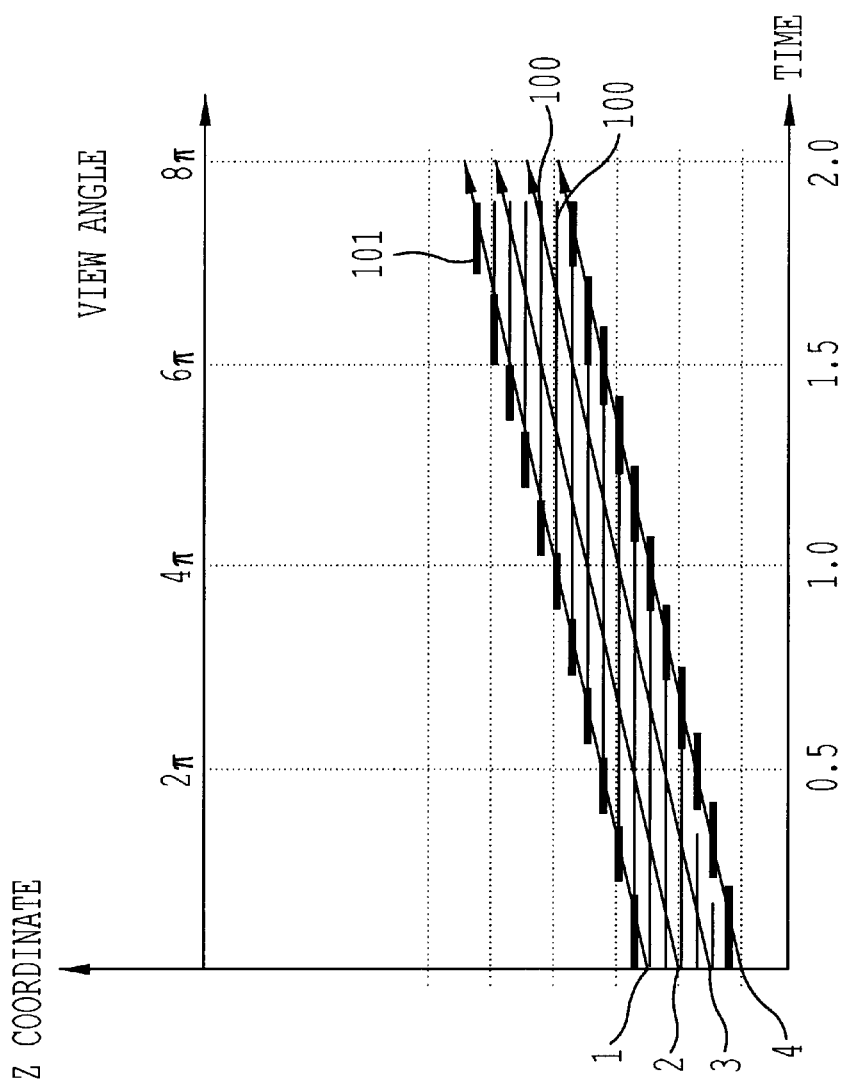

COMPUTED TOMOGRAPHY SYSTEM AND METHOD

BACKGROUND OF THE INVENTION

1. Field of the Invention

The present invention is related to helical scan computed tomography and, in particular, to helical scan computed tomography with improved temporal resolution. The temporal resolution may be improved in each slice image by using an image reconstruction algorithm for multi-slice helical CT which does not need any special signals obtained from a patient.

2. Discussion of the Background

Helical scanning computed tomography (CT) is described, for example, in U.S. Pat. No. 4,630,202. Helical scan CT may incorporate a multi-row detector array to collect data at multiple slice positions, as described in U.S. Pat. No. 4,965,726. Multi-slice helical CT uses such an array. This enables one to improve spatial resolution in the longitudinal direction, to extend the scanning length and to shorten scanning time, which results both in better temporal resolution in volume and better contrast resolution. If the helical scanning is repeated for the same volume, it is possible to observe a temporal variation of the volume.

Various image reconstruction algorithms are used in multi-slice helical CT, such as Algorithm for Image Reconstruction in Multi-Slice Helical CT, Taguchi et al, Med. Phys. 25:550–561 (1998). This algorithm includes a scanning technique consisting of three parts: (1) scanning by optimized sampling scanning whose helical pitch must be carefully selected; (2) interpolation by helical filter interpolation (HFI) which refers to a filtering process in the longitudinal direction, and (3) reconstruction by fan-beam filtered backprojection (a common fan-beam reconstruction technique may be applied in the third step). HFI uses longitudinal filtering for obtaining data at the slice position using either data separated by 180° or 360°, that is, data which is acquired at different time, in the linear interpolation (or extrapolation).

In the optimized sampling scanning, some specific helical pitches (i.e., even integers) should be avoided because the longitudinal data sampling patterns at the central rays are sparse at those helical pitches, which may degrade the image quality in the absence of additional technique. The helical interpolation, HFI, can be described by the following two steps: 1) repeating two-point linear interpolation (or extrapolation) for obtaining plural re-sampled data at positions within "filter-width" and 2) filtering the re-sampled data. Therefore, HFI results in interpolation or extrapolation, depending on the data sampling positions, when filter width equals zero. Filter width is defined as the ratio of the longitudinal range to the nominal slice thickness.

Special methods have been developed for cardiac imaging with multi-slice helical CT to improve practical temporal resolution, but have some disadvantages. For example, they need an EKG signal to re-sort the data for the same cardiac phase and can only be applied by cyclically moving objects.

In parallel-beam geometry the minimal angle of the required projections for image reconstruction is 180°. In fan-beam geometry, the projection data spanning 180°+fan-angle contain such data. However, some projections are measured twice in the projection data and might cause artifacts in the absence of additional process. In order to eliminate the effect of such redundancy and to avoid data truncation, smoothing weight is applied to the projection data sets prior to fan-beam image reconstruction. This algorithm, called half-scanning (HS), has been used to improve the temporal resolution of images in axial CT, as described in Computed Tomography Scanning with Simultaneous Patient Translation, C. Crawford et al., Med. Phys., 17:967–982 (1990).

Other methods that have been used are under-scanning (US), described in Computed Tomography Scanning with Simultaneous Patient Translation, C. Crawford et al., Med. Phys., 17:967–982 (1990). and high temporal resolution reconstruction (HTRR), described in High Temporal Resolution Reconstruction for Reducing Motion Artifact Caused by Cardiac Motion, Shen et al, Jap. J. of Rad. Tech., 54(11): 1287–1294 (1998). The difference among HS, US and HTRR is simply the weighting function, which is shown in FIG. 1. Another method called modified US refers to a weighting technique between "direct" and "complimentary" data considering the acquisition timing, and is shown in FIG. 2.

Other techniques, electron beam CT (EBCT) and EKG gated reconstruction in general purpose CT, are used to improve the temporal resolution. EBCT gives the best temporal resolution, 0.05 sec. in its shortest scanning time. However, EBCT has the disadvantages of insufficient longitudinal spatial resolution, system cost, and limited X-ray exposure. Thus, cardiac imaging with multi-slice helical CT, which does not suffer from these problems, has potential value in cardiac imaging.

Recently, EKG gated reconstruction methods with small helical pitch, which sort helical data according to cardiac cycle phase, have been developed for general purpose CT and have shown promise in obtaining better temporal resolution. With helical multi-slice pitch of 1.0, they can achieve 0.06 sec. at FWTM or at FWTA. The biggest advantage of these dedicated cardiac reconstruction methods is the possibility for dynamic volumetric heart imaging during the whole heart cycle. Spatial resolution and image noise may be improved using data separated by 180 and 360 degrees only if their heart phases match. The two biggest problems of this method are that it can be a high dose examination with small helical pitch, and potential problems exist for studies with contrast agents. Since they utilize data obtained at the same cardiac phase but at the different time, changes other than cardiac motion, such as the contrast concentration, can degrade image quality.

The temporal resolution of individual images obtained with methods such as described above are insufficient for rapidly moving organs such as the heart and adjacent pulmonary vessels. There is a need for better temporal resolution in helical CT and in multi-slice helical CT.

SUMMARY OF THE INVENTION

It is an object of the present invention to provide a method and system to improve temporal resolution in computed tomography (CT).

It is another object of the invention to provide a method and system to improve temporal resolution in multi-slice helical CT.

It is a further object of the invention to provide improved spatial resolution in CT.

It is yet another object of the invention to provide automatic cardiac volumetric reconstruction in CT.

A still further object of the invention to provide a CT method and system to reconstruct images at different timing.

A yet still further object of the invention is to reduce patient dose.

These and other objects are obtained by a computed tomograph method including steps of exposing a subject to x-rays, collecting data corresponding to an image of the subject, processing the data using at least a portion of data obtained simultaneously, weighting the processing data as a function of data collection timing and reconstructing the image of the subject. The process data may be obtained using only a portion of the data obtained simultaneously. Processing the data may consist of at least one of linear interpolation and extrapolation or at least one of non-linear interpolation and extrapolation.

Complementary data may also be obtained and a weighted summation of the process data and the complementary data may be obtained based on the data collection timing. The image is then reconstructed using the weighted summation.

The weighting of the process data may also be shifted temporally. Also, a signal may be obtained from the subject and a timing for the reconstructing the image may be shifted using the signal. The irradiation of the subject may also be controlled using this signal.

Data may be simultaneously obtained for a plurality of rows of data. Selected ones of the rows of data may be processed to yield the processed data. Data may be selected from the rows closest to portions of a slice being reconstructed for each portion, and the data corresponding to each of the portions may be processed to yield process data. The data may be selected from two of the rows closest to the portions of the slice.

Processing the data may also comprise filtering the data to obtain filtered data, and the weighting may comprise weighting the filter data.

The objects of the invention may also be achieved by computed tomograph system having a radiation source, a detector arranged to receive radiation from the source, a processing circuit for processing data obtained from the detector, a data collection timing weighting circuit connected to the interpolation circuit, and a reconstruction circuit connected to the weighting circuit. The processing circuit may comprise at least one of a non-linear interpolation and an extrapolation circuit, or one of a linear interpolation and an extrapolation circuit. The processing circuit may also comprise a filter circuit. The weighting circuit may comprise means for temporally shifting a weighting function or means for selectively temporally shifting the weighting function.

BRIEF DESCRIPTION OF THE DRAWINGS

A more complete appreciation of the invention and many of the attendant advantages thereof will be readily obtained as the same becomes better understood by reference to the following detailed description when considered in connection with the accompanying drawings, wherein:

FIG. 6A is a block diagram of the processing unit of FIG. 3;

FIG. 6B is a block diagram of the processing circuit of FIG. 6A;

FIG. 7 is a diagram illustrating a modified HFI process and weighting of the data according to the present invention;

FIG. 8 is a diagram illustrating channel doubling according to the present invention;

FIGS. 9A and 9B are diagrams of time-shifting according to the invention

FIG. 21 is a diagram with sections (a)–(i) illustrating simulated phantom images at 60 cycles per second

FIG. 28 is a diagram illustrating volumetric reconstruction according to the invention.

DESCRIPTION OF THE PREFERRED EMBODIMENTS

Figure 1:
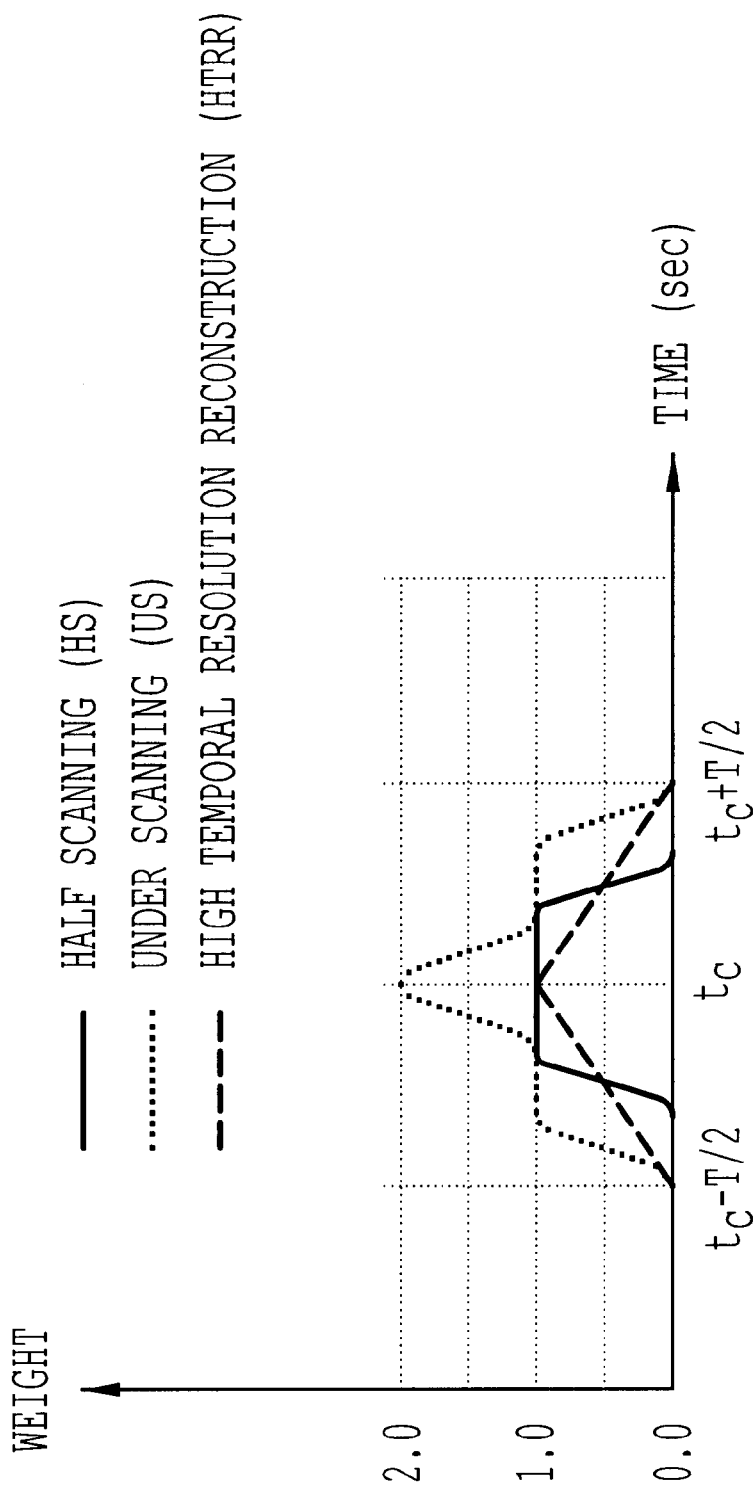
FIG. 1 is a diagram of conventional weighting functions.
Figure 2:
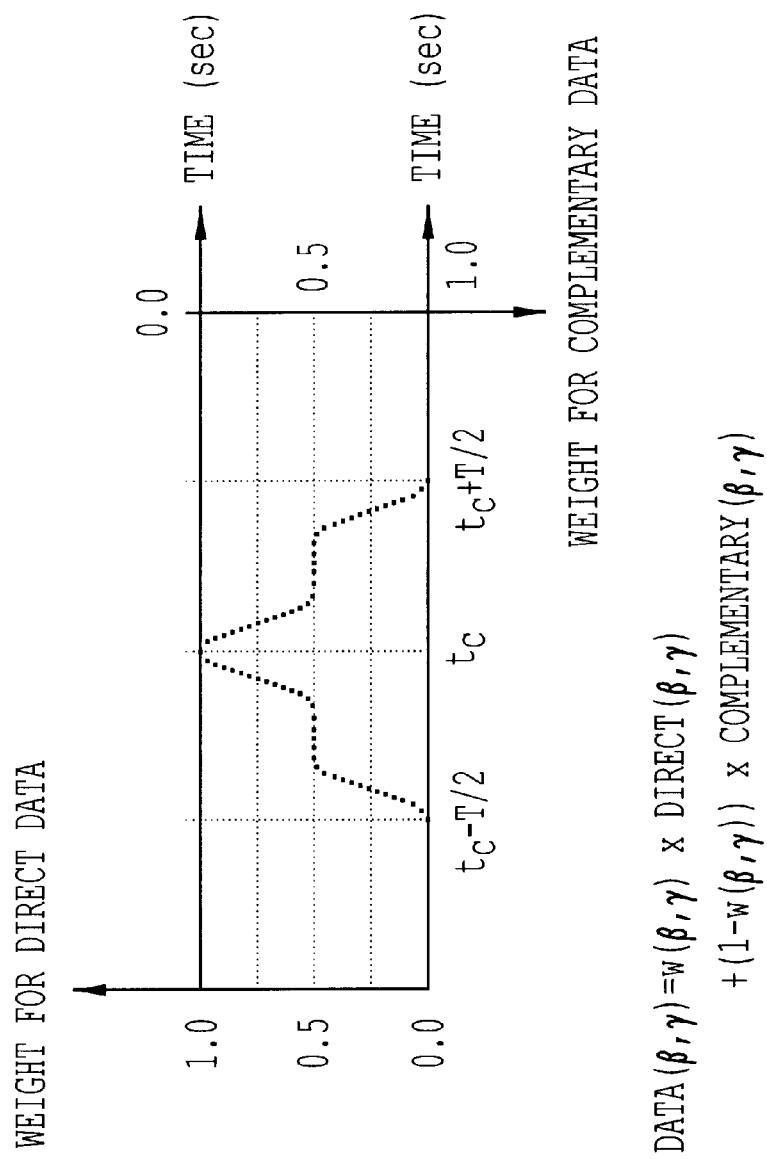
FIG. 2 is a diagram showing the weighting for a modified US technique.

Referring to FIG. 1, helical CT scanning according to the first embodiment of the invention will be described. While it is noted that the present invention may be applied to multi-slice helical CT with any number of slices, four-slice helical CT is discussed here merely as a representative example. As background, in this application slice thickness is defined as the effective slice thickness of each slice image in step-and-shoot scanning which is measured at the isocenter (the rotation axis). As is the case with single-slice CT scanners, the effective slice thickness of the reconstructed image will be different from the geometrical slice thickness in the case of helical scanning, depending on the choice of reconstruction algorithms and parameters. In this application helical slice pitch (P) is defined as the ratio of table movement per rotation to the slice thickness.

Figure 3:
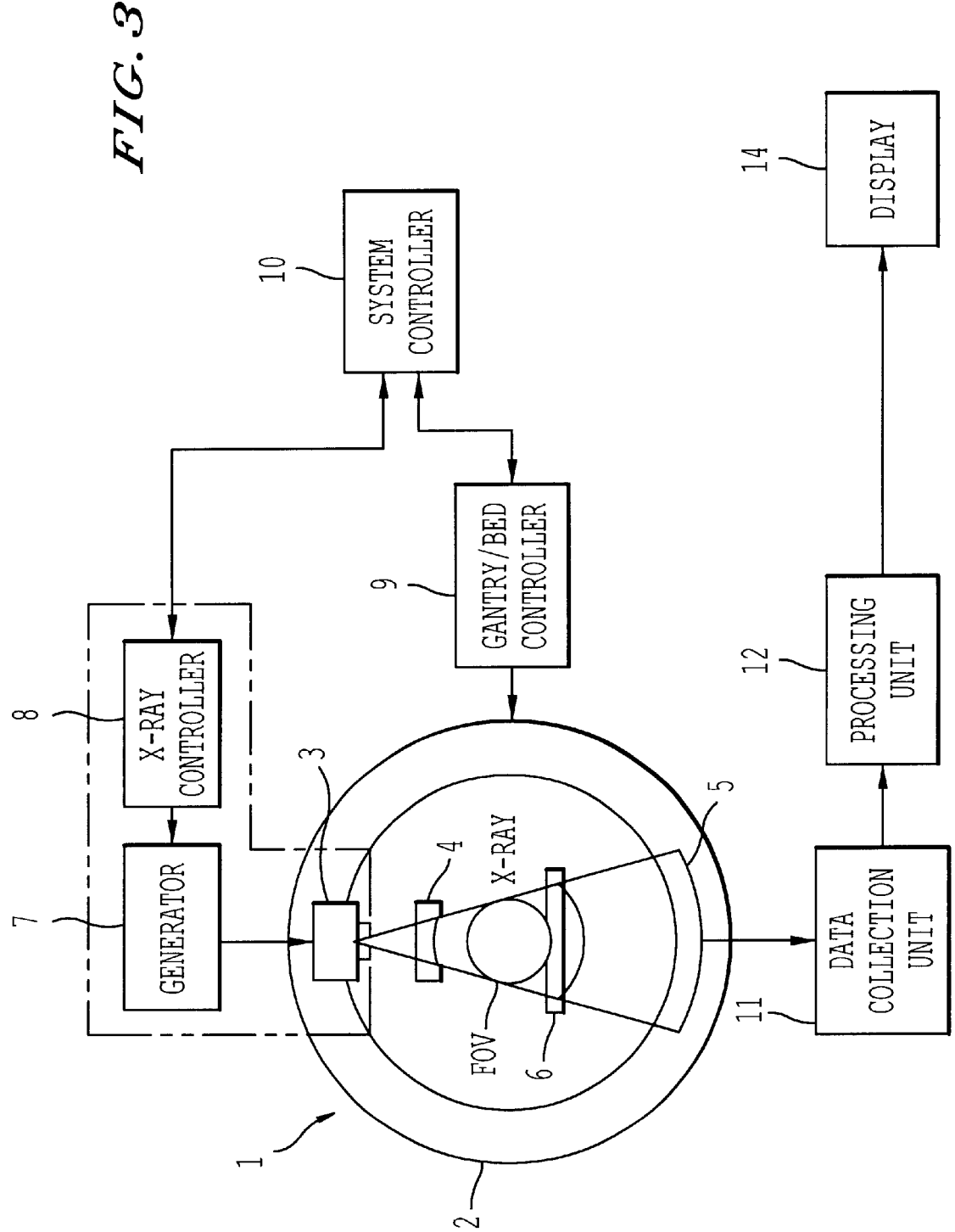
FIG. 3 is a diagram of the system according to the invention.
Figure 4:
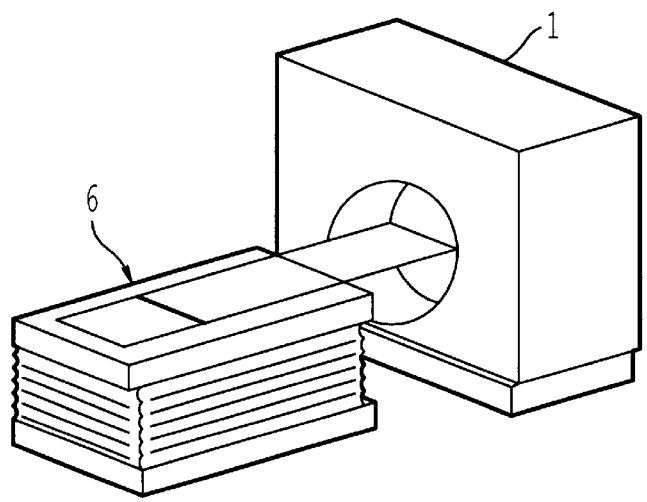
FIG. 4 is a perspective view of the gantry of FIG. 3.
Figure 5:
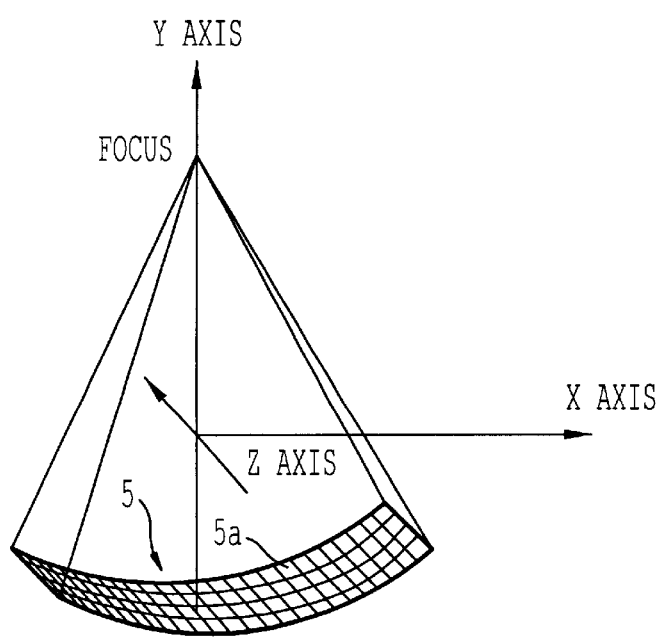
FIG. 5 is a diagram of a multi-slice detector.

The system according to the invention is shown in FIG. 3 which shows an x-ray computed topographic imaging device according to a first embodiment of this invention. FIG. 4 is a perspective view of the gantry of FIG. 3 and FIG. 5 is a perspective view of a two-dimensional array type detector of FIG. 3. The projection data measurement system accommodates an x-ray source 3 that generates a cone-beam of x-ray flux approximately cone-shaped, and a two-dimensional array type x-ray detector 5 consisting of a plurality of detector elements 5A arranged in two-dimensional fashion, i.e., a plurality of elements arranged in one dimension stacked in a plurality of rows. In FIG. 4, four rows each having a plurality of elements are shown (other arrangements are possible), with the x-ray flux shown schematically emitted from focal point F.

X-ray source 3 and two-dimensional array type x-ray detector 5 are installed on a rotating ring 2 in facing opposite sides of a subject, who is laid on a sliding sheet of a bed 6. Two-dimensional array type x-ray detector 5 is mounted on rotating ring 2. Each detector element will correspond with one channel. X-rays from x-ray source 3 are directed on to subject through an x-ray filter 4. X-rays that have passed through the subject are detected as an electrical signal by two-dimensional array type x-ray detector 5.

X-ray controller 8 supplies a trigger signal to high voltage generator 7. High voltage generator 7 applies high voltage to x-ray source 3 with the timing with which the trigger signal is received. This causes x-rays to be emitted from x-ray source 3. Gantry/bed controller 9 synchronously controls the revolution of rotating ring 2 of gantry 1 and the sliding of the sliding sheet of bed 6. System controller 10 constitutes the control center of the entire system and controls x-ray controller 8 and gantry/bed controller 9 such that, as seen from the subject, x-ray source 3 executes so-called helical scanning, in which it moves along a helical path. Specifically, rotating ring 2 is continuously rotated with fixed angular speed while the sliding plate is displaced with fixed speed, and x-rays are emitted continuously or intermittently at fixed angular intervals from x-ray source 3.

The output signal of two-dimensional array type x-ray detector 5 is amplified by a data collection unit 11 for each channel and converted to a digital signal, to produce projection data. The projection data that is output from data collection unit 11 is fed to processing unit 12. Processing unit 12 uses the projection data reconstruct the image. The three-dimensional image data or tomographic image data compiled by unit 12 is sent to display device 14, where it is displayed visually as a three-dimensional image or tomographic image.

The construction of unit 12 is shown in FIG. 6A. Unit 2 includes a processing circuit 20 to perform any necessary filtering, interpolation or extrapolation of the projection data. The data is typically filtered (such as longitudinally) or is linearly interpolated and/or extrapolated. A more detailed view of the processing circuit is shown in FIG. 6B. Data may be input to input 26 and then filtered, interpolated or extrapolated, as needed, with circuits 23, 24 and 25, respectively. The processed data may be output on output 27.

A weighting circuit 21 determines and applies weights to the data processed in circuit 20. A reconstruction circuit 22 reconstructs the image using the weighted data. The operation of the circuits will be described below in connection with the discussion of the method according to the invention.

Various elements of the system of FIG. 3 may be implemented as a programmed computer. In particular, the system controller 10 and processing unit 12 may be separate computers or the functions of the two elements may be carried on a single computer. Also, the invention may be implemented in the form of software, preferably stored on a recordable medium such as a magnetic of optical disk to yield a computer program product.

The first embodiment of the method according to the invention will now be described, and is termed HHS (Helical Half Scanning). First, modified HFI is performed on the projection data followed by weighting the filtered projection data and performing fan-beam reconstruction using the weighted data. Referring to FIG. 7, the modified HFI method uses only data acquired simultaneously in the longitudinal filtering of the data for the slice position, indicated as 30. The data is determined using interpolation (linear or non-linear) and/or extrapolation of the vertical data. The slice position is shown as the solid narrow line. The data (31) illustrated by the oblique thick black lines are used in the interpolation and/or extrapolation to obtain the data to yield the slice. The equations for determining the z interpolation are provided below:

$$v_c \frac{z - zi}{p} \times nv$$

for $$(v_c - kv \leq v \leq v_c + kv)$$

$$\begin{cases} \beta = \frac{2\pi}{nv} \times \beta_i \\ \beta_c = \frac{2\pi}{nv} \times v_c \times \beta_i \\ DataForSlice(\beta, \gamma, z) = Direct(\beta, \gamma, zj) \times \frac{z - zk}{zj - zk} + \\ \qquad\qquad Direct(\beta, \gamma, zk) \times \frac{zj - z}{zj - zk} \end{cases} \quad \text{Eq. (1)}$$

where:

zi is the position of the x-ray source at the first view;

zj and zk are the sampling position of the data which is the closest and the next closest to he slice position obtained at the vth view, view angle β and channel angle γ, repsectively;

β is the view angle at the first view;

p is the helical slice pitch;

nv is the number of views per one tube rotation; and kv is the range where interpolation/extrapolation/filtering is possible.

Data obtained simultaneously means data imaged and detected at the same time. In this example, four rows of data are taken simultaneously, and are indicated as the first-–fourth rows in FIG. 7. The slice is interpolated and/or extrapolated from data acquired simultaneously in the two closest rows in this example. For example, in FIG. 7 the first and second rows are used to interpolate and/or extrapolate the data in the second half of the first rotation. Other choices may be made in the selection of the data used to obtain the slice, i.e. using all four rows. Note that neither data attained 180° away or data in a different rotation is used in this method.

Next, the filtered data are weighted based upon the data collection time. Weighting curve 32 is illustrated in FIG. 7. However, either of the weighting functions developed for HS or US for step-and-shoot may be applied. These two functions are provided below as Eqs. 2 and 3:

After redefine $\beta = \beta - \beta_c + \dfrac{\pi + 2\gamma_m}{2}$ Eq. (2)

Weights $\omega(\beta,\gamma)$ satisfying may be applied (these equations are shown in Appendix C of Crawford et al, incorporated herein by reference):

$$\omega(\beta, \gamma)+\omega(\beta+\pi+2\gamma, -\gamma)=1$$

such as $$\omega[x(\beta, \gamma)]=3x^2(\beta, \gamma)-2x^3(\beta, \gamma)$$

where $$x(\beta, \gamma) = \begin{cases} \dfrac{\beta}{2\gamma_m - 2\gamma} & 0 \le \beta \le 2\gamma_m - \gamma \\ 1 & \gamma_m - 2\gamma \le \beta \le \pi - 2\gamma \\ \dfrac{\pi + 2\gamma_m - \beta}{2\gamma_m + 2\gamma} & \pi - 2\gamma \le \beta \le \pi + 2\gamma_m \end{cases}$$

Also, the following may be used $$\omega(\beta, \gamma) = \begin{cases} 1 & 0 \le \beta \le 2\gamma_m - \gamma \\ 0 & \pi - 2\gamma \le \beta \le \pi + 2\gamma_m \end{cases}$$

$$\omega(\beta, \gamma) = \begin{cases} 1 & 0 \le \beta \le \pi - 2\gamma \\ 1 - f\left(\dfrac{\gamma - \gamma_0(\beta)}{d} + \dfrac{1}{2}\right) & \pi - 2\gamma \le \beta \le \pi + 2\gamma_m \end{cases}$$

where $\gamma_0(\beta) = (\pi-\beta)/2$ and, for example, $$f(\gamma) = \begin{cases} 0 & \gamma < 0 \\ 3\gamma^2 - 2\gamma^3 & 0 \le \gamma \le 1 \\ 1 & \gamma > 1 \end{cases}$$

For Equation 3:

After redefine $\beta=\beta-\beta_c+\pi$ Eq. (3)

and the following weights may be applied (these equations shown in Appendix B of Crawford et al, incorporated herein by reference):

$$\omega(\beta,\gamma)+\omega(\beta+\pi+2\gamma, -\gamma)=2$$

If complimentary data is generated, any weighting function may be applied such as the following:

DataForRecon($\beta,\gamma,z$)=DataForSlice($\beta,\gamma,z$)×$w(\beta,\gamma)$+DataForSlice-Complementary($\beta,\gamma,z$)×(1−$w(\beta,\gamma)$)  Eq. (4)

where DataForSliceComplementary is data generated from DataForSlice. This method of weighting may be easier to implement but it may be more expensive computation-wise.

The method then includes a step of common fan-beam reconstruction. Other approaches such as fan-to-parallel rebinning followed by parallel-beam reconstruction may be applied. To reduce the number of calculations, only the range whose weighting function value is not zero may be calculated in the helical interpretation in the first step.

FIG. 8 illustrates channel doubling which may be optionally applied to the embodiment described above. Sampling positions of the complimentary data are shifted in an x-y plane from those of the direct data by half the sampling pitch. Since the X-ray paths of the complimentary data are shifted from the direct data, the spatial resolution in the axial plane may be increased. Keeping the number of channels the same and reducing the sampling pitch of the data in the axial plane (channel direction) may provide similar results (improving the spatial resolution, when the object is small enough). The data for the slice is given by the following equation $$DataForSlice\left(\beta, \gamma + \dfrac{d\gamma}{2}, z\right) = \dfrac{DataForSlice(\beta, \gamma, z) + DataForSlice(\beta, \gamma + d\gamma, z)}{2}$$  Eq. (5)

The channel doubling may be applied to the above embodiment with or without weighting of the complementary data. In other words, without weighting the complementary data (using, for example, Eqs. 2 or 3) Eq. 5 is applied and when the complementary data is weighted, Eq. 5 is applied before applying Eq. 4.

Figure 9B:
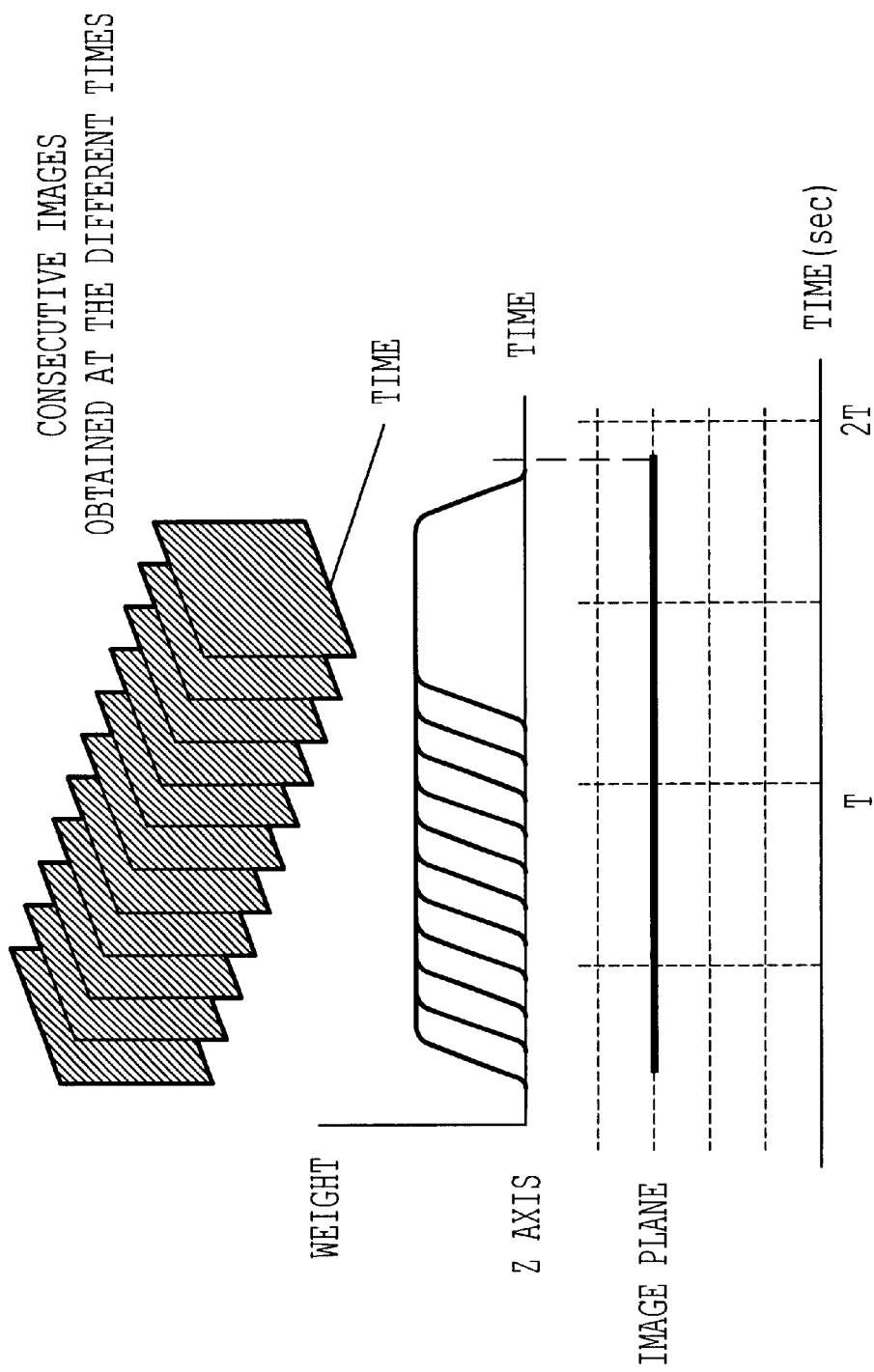

In a second embodiment, images are reconstructed at a same table position but at different timing. This embodiment may also be applied optionally to that described for the embodiment above, and the embodiment above including channel doubling. This embodiment, a "timing shift" (TS) technique shifts the weighting function along the temporal axis, as shown in FIGS. 9A and 9B. The amount of the time shift is determined by the demands of particular applications, or the quality of the reconstructed image needed. For example, a smaller time shift may be selected to increase the reconstructed image quality, but the computational expense is increased. When only a general shape of a reconstructed image is needed a larger (or maximum) time shift may be selected.

Here, $t_c$ and $t_o(z_s)$ refer to the time corresponding to the center of the range and the time the X-ray focus goes across the slice plane ($z=z_s$), respectively. The standard data range is defined where $t_c=t_o(z_s)$. The timing shifted from $t_o(z_s)$ and the maximum of the shifted timing are defined as $t_s$ and $t_{sm}$, respectively. Since either a large absolute value of $t_s$ or P results in degraded image quality with extraordinary extrapolation, $t_{sm}$ may be limited to using extrapolation within half of a slice thickness as shown in FIG. 9A. Equation 6, provided below, gives $t_{sm}$ with various P and reconstruction algorithms.

[Maximum shift time] = $\pm t_{sm}$ =   Eq. (6)

$$\pm \dfrac{[\text{Slice covered time}] - \text{Necessary time for half or under scanning}]}{2}$$

$$t_{sm} \begin{cases} \dfrac{\left(\dfrac{(n-k)}{p} - \dfrac{\pi + 2\gamma_m}{2\pi}\right) \cdot Trot}{2} & \text{Helical Half Scanning} \\ \dfrac{\left(\dfrac{(n-k)}{p} - 1\right) \cdot Trot}{2} & \text{Helical Under Scanning} \end{cases}$$

where $k = \begin{cases} 0 & \text{extrapolation of nearest neighbor within half slice thickness} \\ 1 & \text{interpolation only} \\ 1 + fw & z \text{ filtering with a filter width of } fw \end{cases}$ Reconstructing each slice as described above may be used in conjunction with a technique to achieve automatic cardiac volumetric reconstruction. The EKG signal is archived when helical data is obtained. The central timing ($t_c$) for each slice is adjusted in order to (1) avoid the systolic phase and/or (2) to select a data range obtained by the least cone angle. This is illustrated in FIGS. 10 and 11.

Figure 10:
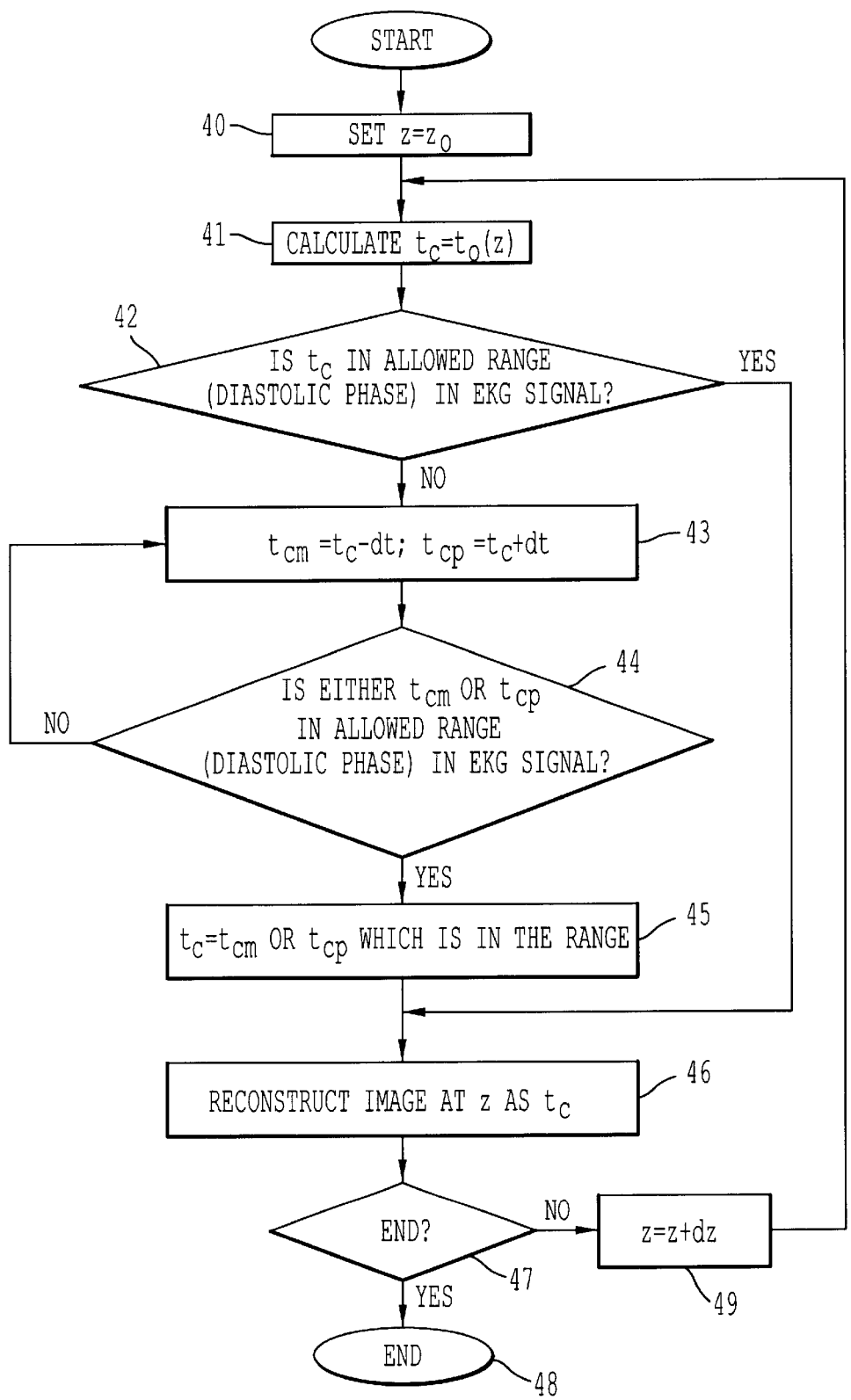
FIG. 10 is a flow chart illustrating reconstructing images with EKG gating according to the invention.
Figure 11:
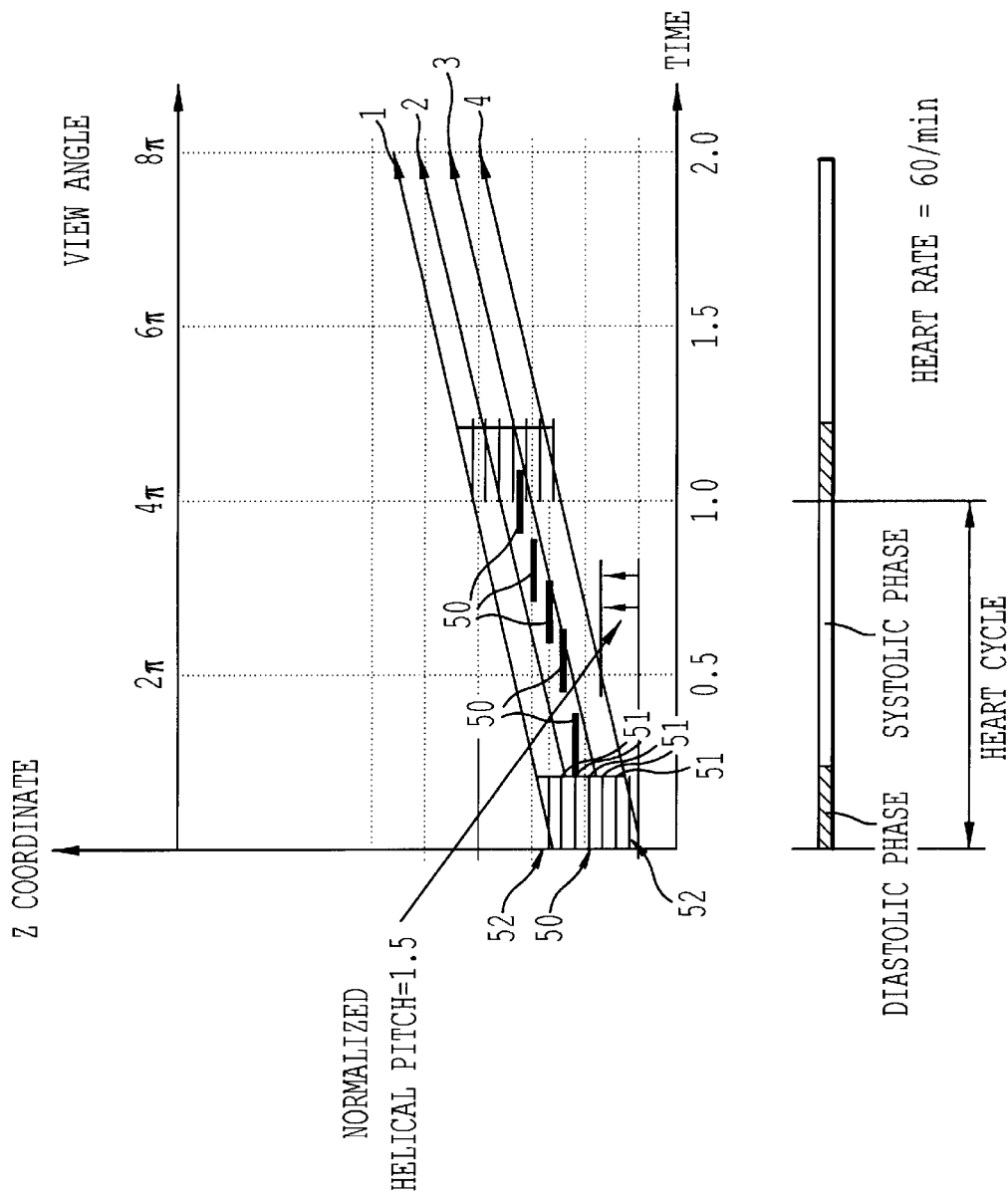
FIG. 11 is a diagram of reconstructing an image according to the invention.

In the method of FIG. 10, z is set to $z_0$ in step 40 and, in step 41, the central timing $t_c$ is calculated as $t_o(z)$. It is then determined, in step 42, if $t_c$ is in the allowed range in the EKG signal, i.e., in the diastolic phase. If yes, the method proceeds to step 46 where the image is reconstructed at z with $t_c$. If no, the method proceeds to step 43 where $t_{cm}$ and $t_{cP}$ are calculated. In step 44 it is determined whether $t_{cm}$ or $t_{cP}$ are in the allowed range (diastolic phase) in the EKG signal. If yes, then $t_c$ is set to $t_{cm}$ to $t_{cP}$ which is in the range (step 45) and the image is reconstructed at z with $t_c$. If no in step 44, then $t_{cm}$ and $t_{cP}$ are again calculated and it is again checked whether $t_{cm}$ or $t_{cP}$ is in the allowed range.

In step 47 it is determined whether the procedure has come to an end. If yes, the procedure terminates in step 48 if not, z is incremented by dz (step 49) and the procedure returns to step 41 to recalculate $t_c$ at the new value of z. FIG. 11 illustrates reconstructed images using data obtained in the diastolic phase. In FIG. 11, reference numeral 50 represents a reconstructed slice with the least cone angle, 51 represents a reconstructed slice using only interpolation, and 52 represents a reconstructed slice using interpolation and/or extrapolation.

Figure 12:
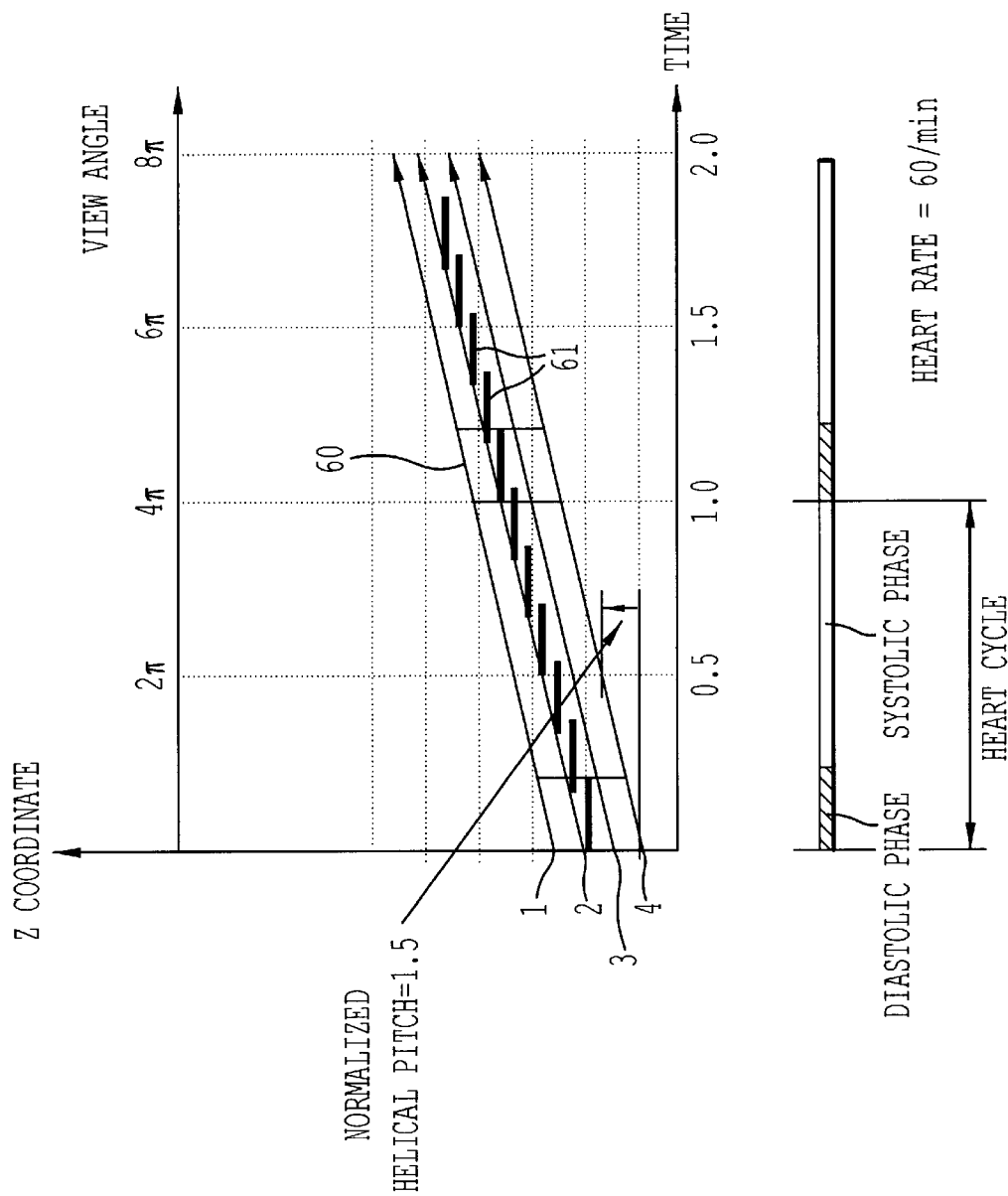
FIG. 12 is a diagram of reconstructing images with selective timing according to the invention.

It is also possible to perform the method where all slices are reconstructed with $t_c$ equal to $t_0$ ($z_s$) at first, and then images are reconstructed for different timing when an operator indicates which slices are to be taken. This is illustrated in FIG. 12. Reference numeral 60 represents the data taken in the diastolic phase and reference numeral 61 represents a reconstructed slice using only interpolation.

Figure 13:
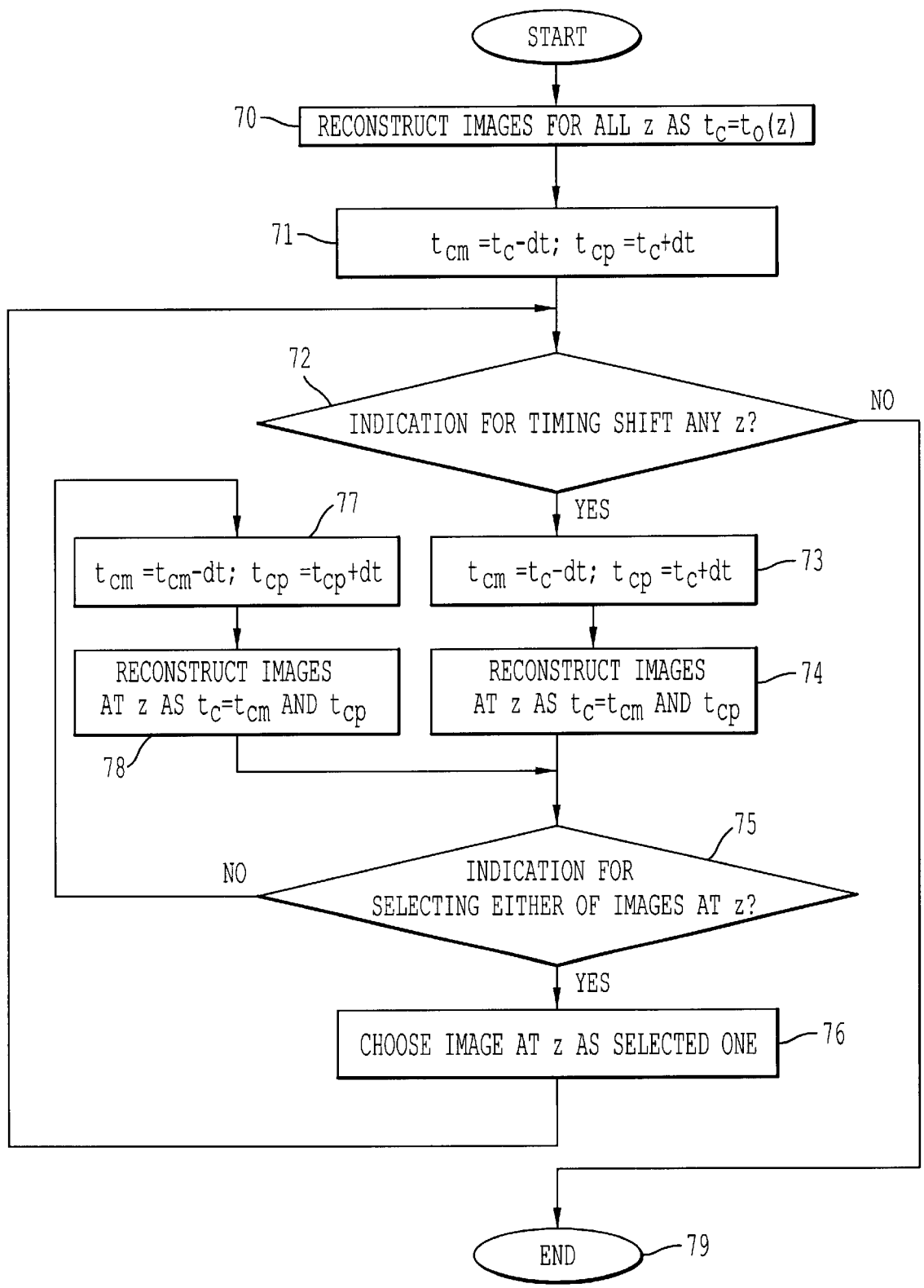
FIG. 13 is a flow chart of the method illustrated in FIG. 12.

A flow chart of this method is shown in FIG. 13. In step 70, all images are reconstructed at $t_c = t_o(z)$. $t_{cm}$ and $t_{cP}$ are calculated as in step 71 and then it is determined whether there is any timing shift in z in step 72. If no, the method ends in step 79. If yes in step 72, $t_{cm}$ and $t_{cp}$ are recalculated (step 73) and all images are reconstructed at z with $t_c = t_{cm}$ and $t_{cP}$ (step 74) Another check is made (step 95) whether there is any indication of selecting either of the images at z. If there is, the image at z is chosen as a selected image in step 76 and the method returns to step 72. If no in step 75, $t_{cm}$ and $t_{cP}$ are again calculated (step 77) and the images are reconstructed with the new values of $t_{cm}$ and $t_{cP}$ in step 78. Step 78 then returns to step 75.

EXAMPLE

An example of the method according to the invention will now be described. Physical evaluations of the method were performed using computer simulations in order to evaluate the temporal and the spatial (z) resolution, the image noise, and the accuracy of the in-plane image of a moving phantom. The methods performed and compared were HHS with and without TS, and HFI for multi-slice CT, and 180LI for single-slice CT. The geometry and the X-ray tube rotation time were identical to those of a four-slice helical CT scanner (Aquilion; Toshiba Medical Systems Company, Tokyo, Japan), which acquires a full 360° scan with 900 projections in 0.5 sec.

The temporal and spatial (z) resolution, and the image noise were evaluated varying the helical pitch and the filter width for HHS and HFI. In other evaluations, the helical multi-slice pitch was fixed at 2.5 for multi-slice CT and at 1.0 for single-slice CT, respectively, as will be discussed below. The nominal slice thickness was 2.0 mm for spatial resolution, and 1.0 for moving phantom.

Figure 14:
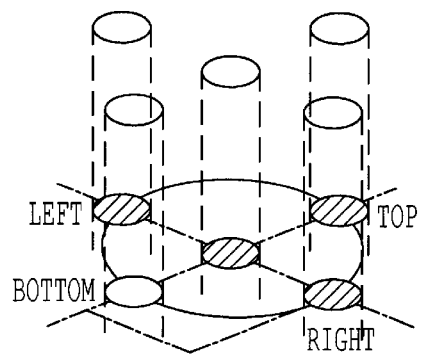
FIG. 14 is a diagram of a phantom used in evaluating the present invention.

First, the temporal resolution was evaluated by determining using a five-cylinder phantom as shown in FIG. 14. The five cylindrical disks have a diameter of 20 mm, infinite height and a contrast of 1000 HU. A temporal sensitivity profile (TSP) was measured, using the following parameters: 9 projections (corresponding to 0.005 sec) for the five-cylinder phantom; reconstruction increment of 0.1 mm; helical multi-slice pitch, 2.5 through 8.0; the filter width, 0.0 and 1.0. Measured FWHMs and FWTMs of the section sensitivity profiles (TSPs) were normalized to those of axial CT (0.5 sec).

Evaluating temporal resolution with TSPs will be discussed. The input projection data, which are all zero except several consecutive projections corresponding to an extremely short time (0.005 sec), can be considered as an impulse signal along the temporal axis. The several projections are obtained using a cylindrical phantom parallel to z-axis, which is long and thick enough to eliminate the effect of spatial resolution. In order to evaluate the spatial dependence of TSPs in the axial images, a phantom with several cylinders at different xy-locations is used (as described above).

Images are reconstructed by z-increment corresponding to a short time (preferably less than about 0.03 sec). The TSP at each location can be obtained by the following procedure using the above described projection data: (1) reconstructing images with a z-increment corresponding to the short time; (2) measuring the mean pixel value of the region of interest (ROI) at the position of each cylinder in all of reconstructed images; (3) normalizing them by the maximum value; and 4) plotting them against the temporal axis. In this example an ROI was selected at the center but other positions are possible.

Figure 15B:
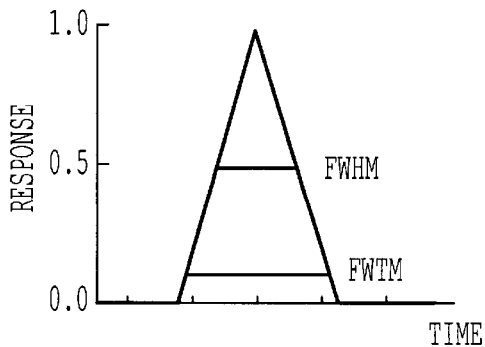
FIGS. 15A and 15B are diagrams of temporal sensitivity profiles.
Figure 15A:
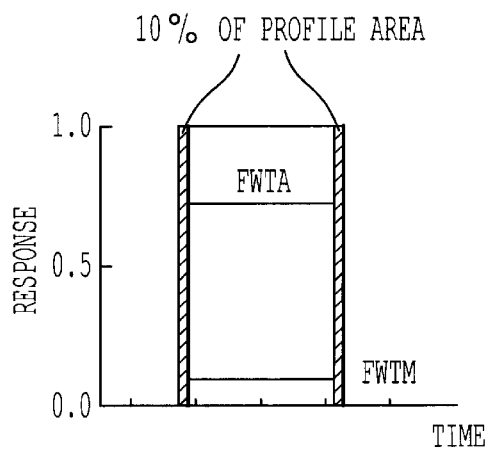

Now how to quantify the temporal resolution using TSPs will be discussed. FIGS. 15A and 15B show two TSPs. The full-width-at-tenth-maximum (FWTM) is a better descriptor of the temporal sensitivity profile than the full-width-at-half-maximum (FWHM) for broad profiles such as FIG. 15A, and should be superior to the full-width-at-tenth-area (FWTA) for rectangular profiles (e.g., FIG. 15B). Therefore, the FWTMs of TSPs is the preferred descriptor to quantify the temporal resolution.

To evaluate the spatial resolution, section sensitivity profiles (SSPs) are preferably used (see Spiral Volumetric CT with Single-Breath-Hold Technique, Continuous Transport, and Continuous Scanner Rotation, Kalender et al, Radiology 176:181–183 (1990)). The SSPs were measured using simulated phantom containing five disks in one axial (x-y) plane (see also FIG. 14). The disks have a diameter of 20 mm and a thickness of 0.2 mm. The multi-slice helical pitch was varied 2.5 through 4.5. Images were reconstructed with a reconstruction increment of 0.1 mm. The FWHMs and the FWTMs of the SSPs were measured and were normalized to those of axial CT. Two SSPs, $HHS_0$ without TS and with $TS_{-0.20}$ at multi-slice helical pitch of 2.5, were compared to evaluate the effect of TS.

Figure 16:
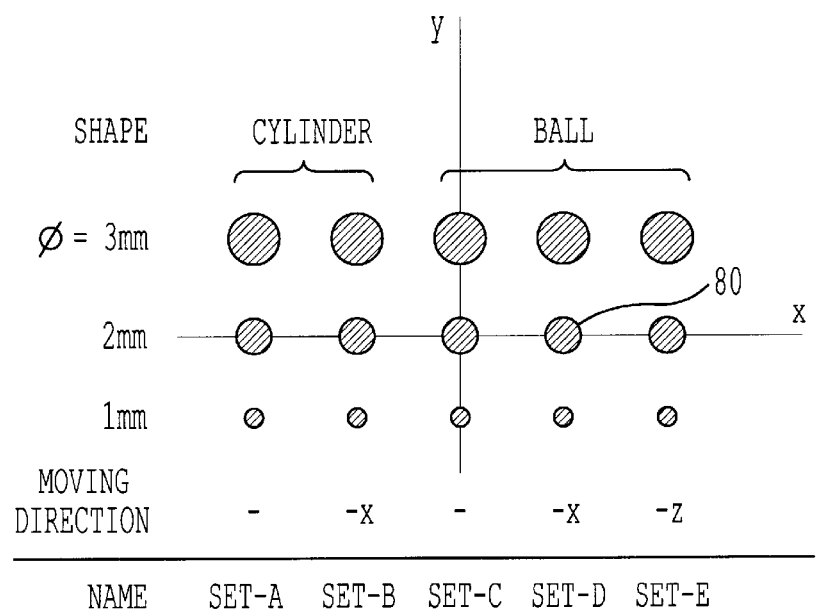
FIG. 16 is a diagram of a moving phantom.
Figure 17:
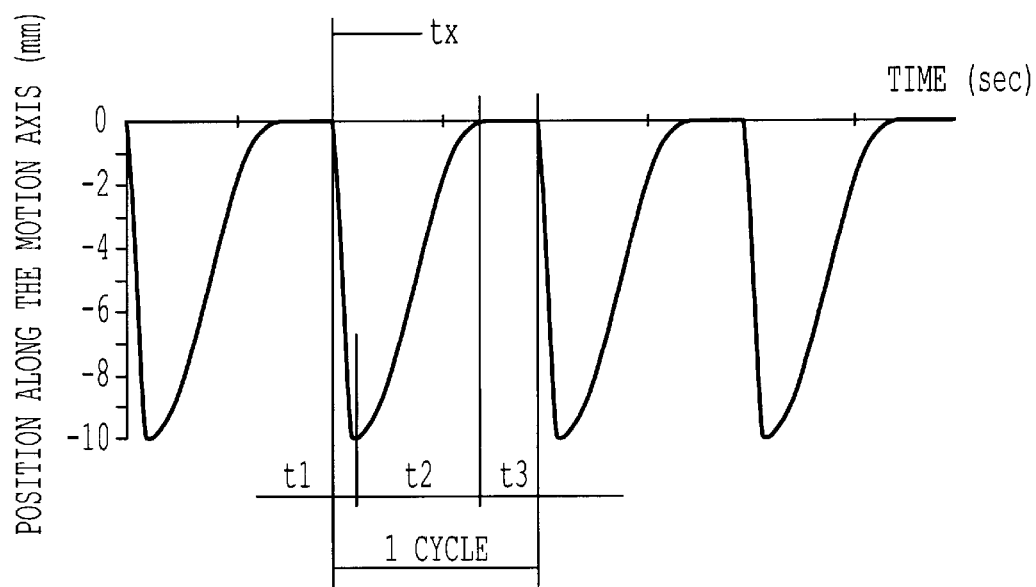
FIG. 17 is a diagram of movement of the phantom of FIG. 16.

The imaging performance for the moving objects of each reconstruction algorithm was evaluated using a moving phantom. The simulated phantom has two sets of cylinders and three sets of balls with contrast of 1000 HU; each set consists of three balls with different diameters, 1, 2, and 3 mm (FIG. 16). The cylinders had an infinite length and all of the balls were centered at plane z=0 when they do not move.

As for the motion pattern, Set-A and Set-C were stationary, and the others moved with frequencies 60 or 90 cycles per minute. Sets B and D move in the x direction, and Set E moves in the z direction. One cycle of motion pattern consists of three parts: (1) moving for 10 mm from the original position (FIG. 16) toward −x or −z direction along a half of the cosine curve in $t_1$ sec., (2) moving back to the original position along a half of the cosine curve in $t_2$ sec., and (3) stationary at the original position for $t_3$ sec. The parameters ($t_1$, $t_2$, $t_3$), in seconds, were (0.08, 0.62, 0.30) for 60 cycles and (0.05, 0.41, 0.20) for 90 cycles per minute, respectively.

The sizes, the shapes, and the motion pattern were chosen simulating a part of the following motions: the heart walls, the pulmonary vessels near the heart, vessel pulsation, the coronary artery, and the coronary artery calcifications. The chosen simple motion pattern does not simulate their specific motions, which consists of complicated three dimensional motion (or distortion) such as shrinking, expanding, twisting, and parallel motion. However, the moving phantom allows the evaluation of the ability to image moving objects in general.

Helical scanning was employed twice, adjusting the time ($t_X$ in FIG. 16) when the X-ray focus crossed the plane z=0 to "stationary phase" and "rapid motion phase," respectively. For the stationary phase, the time was at the center of motion-3 ($t_X$ was 0.85 for 60 cycles and 0.56 for 90 cycles, respectively). For the rapid motion phase, the time was during motion-2 ($t_X$=0.15 sec for both cycles) so that all the data required for HHS were obtained while objects were moving. Therefore, HHS had advantage in the stationary phase, but had disadvantage in the rapid motion phase. Helical multi-slice pitch was fixed at 2.5 for multi-slice CT, and at 1.0 for single-slice CT.

Images at z=0 were reconstructed by $HHS_0$ with and without TS, $HFI_0$, $HFI_1$, and 180LI. In order to quantify the results, the maximum and the minimum value of ROI were measured which was set to include one ball (80 in FIG. 16). The maximum value represents the accuracy of the contrast of the moving object; the minimum value indicates the strength of the artifact.

Physical Evaluation and Phantom Study
(1) Evaluation of Temporal resolution

Figure 18A:
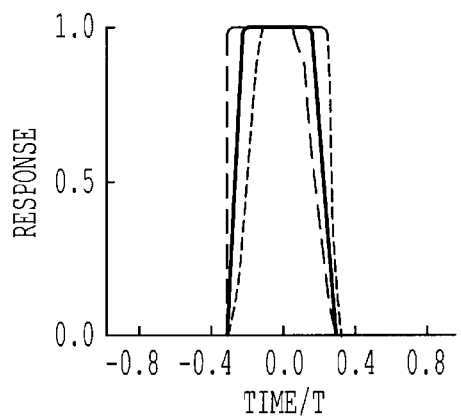
FIGS. 18A–18D are diagrams of temporal sensitivity profiles.

All of the measured temporal sensitivity profiles reflected the weights used for projection data (FIGS. 18A–18D). In FIGS. 18A–18D the center phantom corresponds to the solid line, the right phantom corresponds to the small-dashed line, the bottom and left phantoms correspond to the large-dashed line, and the top phantom corresponds to the small-large-dashed line. It is noted that the curves for the bottom and left phantoms overlap. HHS gave the narrowest TSP which is almost rectangular (FIG. 18A); $HHS_0$ and $HHS_1$ provided identical profiles. Note that the TSP of HHS varies slightly at the base and significantly at the peak, and that the opposite is true for 180LI and HFI. The TSP of $HFI_0$ (FIG. 18B) consists of multiple triangles over a relatively broad range, the response near time-zero is almost zero and that at the other times is intense. The TSP of $HFI_1$ (FIG. 18C) showed that the longitudinal filtering smoothed the profile of $HFI_0$.

Figure 18B:
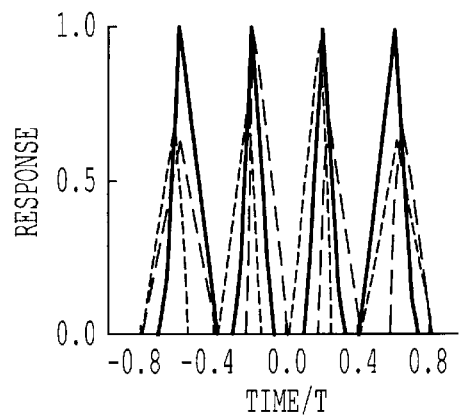
Figure 18C:
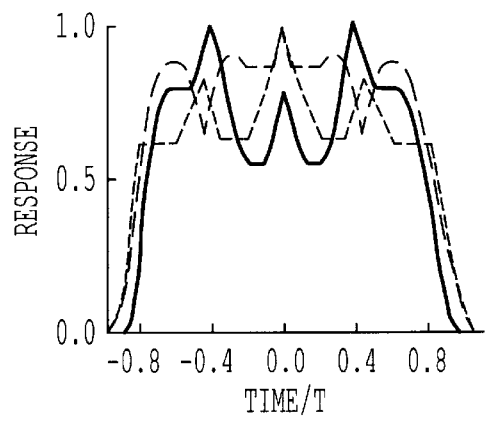
Figure 18D:
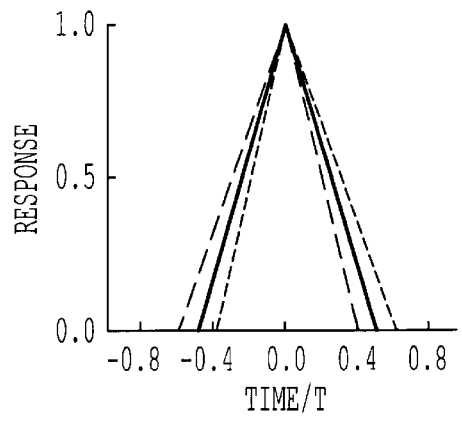

For the curves in FIGS. 18A–18D, a rectangular shape is ideal (FIG. 18A, the method according to the invention, is closest to ideal). A broadening of the curve represents degradation. FIG. 18C shows some broadening, but the response is degraded around 0.0. A complicated triangular shape is very degraded, with the response rapidly changing with time. FIG. 18B shows significant degradation, with the response at −0.4, 0.0 and 0.4 being zero. The response curve of FIG. 18D also is degraded somewhat from the ideal shape.

Figure 19A:
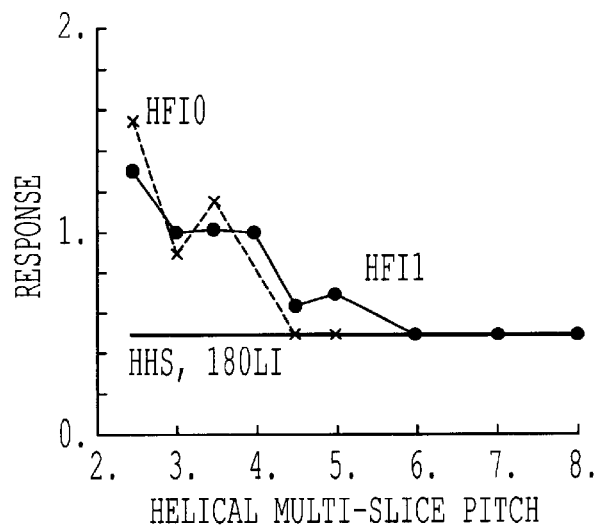
FIGS. 19A and 19B are diagrams of the variation of temporal resolution with helical pitch for FWHM and FWTM, respectively.
Figure 19B:
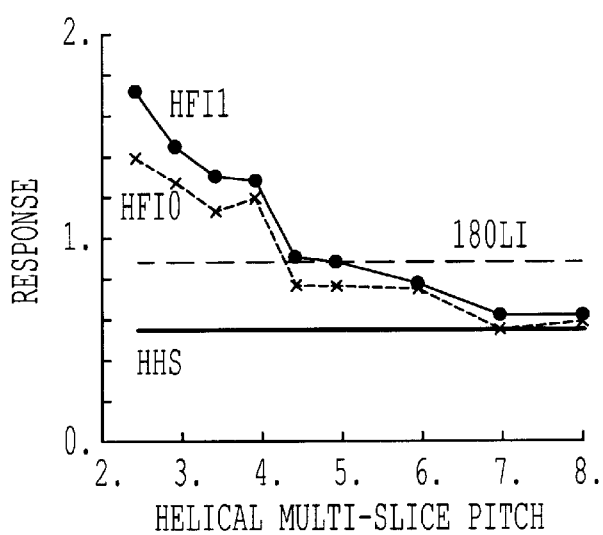

Both FWHM and FWTM of TSPs with HHS were fixed at 0.50 and 0.58 with all helical pitches (see FIGS. 19A and 19B; Table I, below). Table I provides temporal resolution data. FWHM and FWTM data were normalized against those of axial (step-and-shoot) CT. Each corresponds to 0.25 sec. and 0.29 sec. with a 0.5 sec. rotation scanner, respectively, which is better than those of HFI when helical multi-slice pitch is less than 4.5 (FIGS. 19A and 19B). According to the FWTM of TSPs (FIG. 19B), HFI does not show preferable helical pitches with respect to temporal resolution. With HFI, either higher helical pitch or faster tube rotation provides better temporal resolution of axial images in addition to shorter scan times. It is worse than single-slice helical CT (180LI) when helical multi-slice pitch is less than 4.5, but almost the same as HHS when helical multi-slice pitch is equal to or larger than 7.0.

TABLE I

| Helical slice pitch (P) | HHS0 FWHM ratio | HHS0 FWTM ratio | HFI0 FWHM ratio | HFI0 FWTM ratio | HFI1 FWHM ratio | HFI1 FWTM ratio |
|---|---|---|---|---|---|---|
| 2.5 | 0.50 | 0.58 | 1.30 | 1.40 | 1.54 | 1.72 |
| 3.0 | 0.50 | 0.58 | 1.00 | 1.28 | 0.88 | 1.46 |
| 3.5 | 0.50 | 0.58 | 1.02 | 1.14 | 1.16 | 1.32 |
| 4.0 | 0.50 | 0.58 | 1.01 | 1.22 | 1.01 | 1.30 |
| 4.5 | 0.50 | 0.58 | 0.64 | 0.78 | 0.50 | 0.92 |
| 5.0 | 0.50 | 0.58 | 0.70 | 0.79 | 0.50 | 0.90 |
| 6.0 | 0.50 | 0.58 | 0.50 | 0.77 | 0.50 | 0.80 |
| 7.0 | 0.50 | 0.58 | 0.50 | 0.56 | 0.50 | 0.64 |
| 8.0 | 0.50 | 0.58 | 0.51 | 0.61 | 0.51 | 0.65 |

(2) Evaluation of Spatial resolution

For helical half-scanning, the FWHM and the FWTM of the section sensitivity profile simply increased with helical pitch (Table II, below); this tendency was similar to that of single-slice helical CT but was quite different from that of HFI.

Figure 20A:
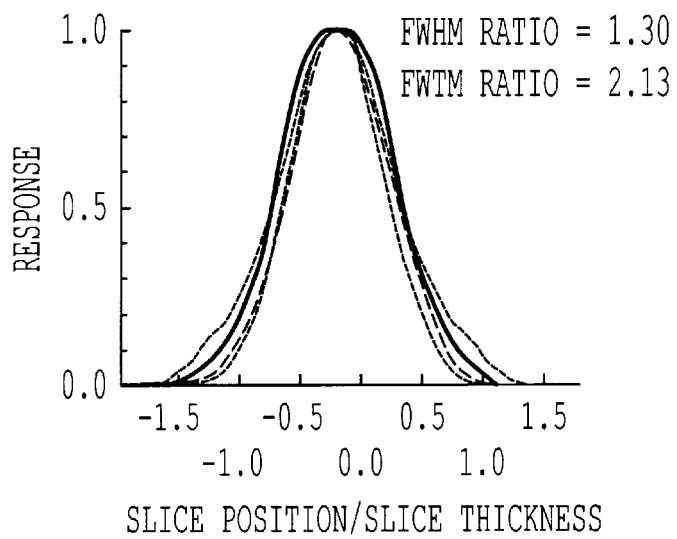
FIGS. 20A and 20B are diagrams of section sensitivity profiles.
Figure 20B:
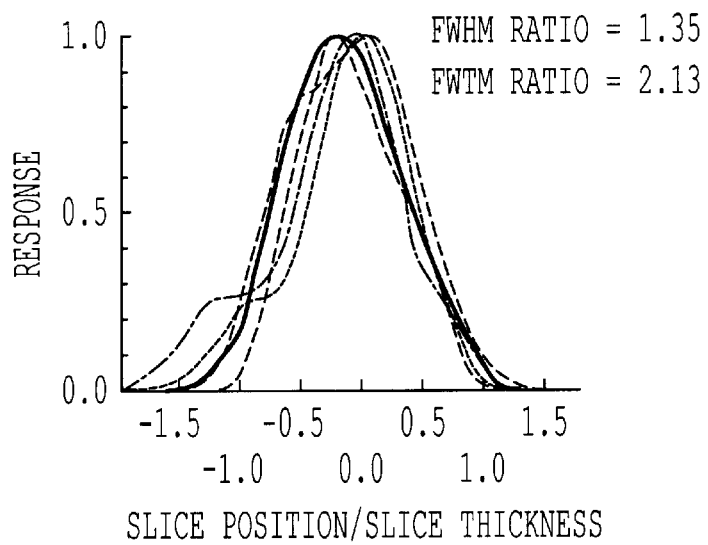

TS did not change the FWHM and FWTM of the section sensitivity profiles significantly, although it affected the shape and increased the spatial variations. FIGS. 20A and 20B illustrate FWHM and FWTM for $HHS_0$ without TS and with $TS_{−0.20}$, respectively. The shape of the lines correspond to the phantoms as described above for FIGS. 18A–18D.

TABLE II

| Helical slice pitch (P) | HHS0 FWHM ratio | HHS0 FWTM ratio | HHS0 Noise ratio | HHS FWHM ratio | HHS FWTM ratio | HHS Noise ratio | HFI0 FWHM ratio | HFI0 FWTM ratio | HFI0 Noise ratio | HFI1 FWTM ratio | HFI1 FWTM ratio | HFI1 Noise ratio |
|---|---|---|---|---|---|---|---|---|---|---|---|---|
| 2.5 | 1.30 | 2.13 | 1.12 | 1.47 | 2.49 | 0.99 | 1.09 | 1.28 | 0.87 | 1.24 | 2.13 | 0.54 |
| 3.0 | 1.32 | 2.09 | 1.13 | 1.62 | 2.63 | 0.99 | 1.11 | 1.51 | 0.79 | 1.30 | 2.09 | 0.58 |
| 3.5 | 1.34 | 2.20 | 1.12 | 1.77 | 2.77 | 0.99 | 1.11 | 1.53 | 0.86 | 1.31 | 2.20 | 0.60 |

TABLE II-continued

| Helical slice pitch (P) | HHSO | | | HHS | | | HFI0 | | | HFI1 | | |
|---|---|---|---|---|---|---|---|---|---|---|---|---|
| | FWHM ratio | FWTM ratio | Noise ratio | FWHM ratio | FWTM ratio | Noise ratio | FWHM ratio | FWTM ratio | Noise ratio | FWTM ratio | FWTM ratio | Noise ratio |
| 4.0 | 1.36 | 2.24 | 1.13 | 1.81 | 2.91 | 0.99 | 1.38 | 2.07 | 0.74 | 1.57 | 2.24 | 0.59 |
| 4.5 | 1.38 | 2.27 | 1.12 | 1.85 | 3.05 | 0.99 | 1.14 | 1.35 | 0.85 | 1.58 | 2.27 | 0.65 |

(3) Evaluation of Noise

Image noise stayed almost constant (Table II); this tendency is also similar to that of single-slice helical CT but is quite different from that of HFI. The noise SD varied 1.08 through 1.24 as the extent of TS changed −0.25 through 0.25 sec. with helical multi-slice pitch of 2.5.

(4) Moving phantom Evaluation

FIG. 21 (having sections a–i) shows the maximum and minimum CT numbers within and around a ball (80 in FIG. 16) in the case of the stationary phase at 60 cycles per minute. HHS showed an artifact free image (a). When the object moved rapidly (e)–(g), HHS without TS (e) generated poor images. $HFI_0$ (f) gave the best performance because it uses data obtained while the object was stationary (see FIG. 18B). The TS technique improved the image quality of HHS (i), drastically improving the accuracy of CT numbers (i), giving the best performance. The helical pitch used was 2.5 for the multi-slice CT and 1.0 for the single slice CT. The nominal slice thickness was 1.09 mm, the phantom contrast was 1000 HU, the background was 0 HU, and the window (width, level) was (1000, 0).

Figure 22:
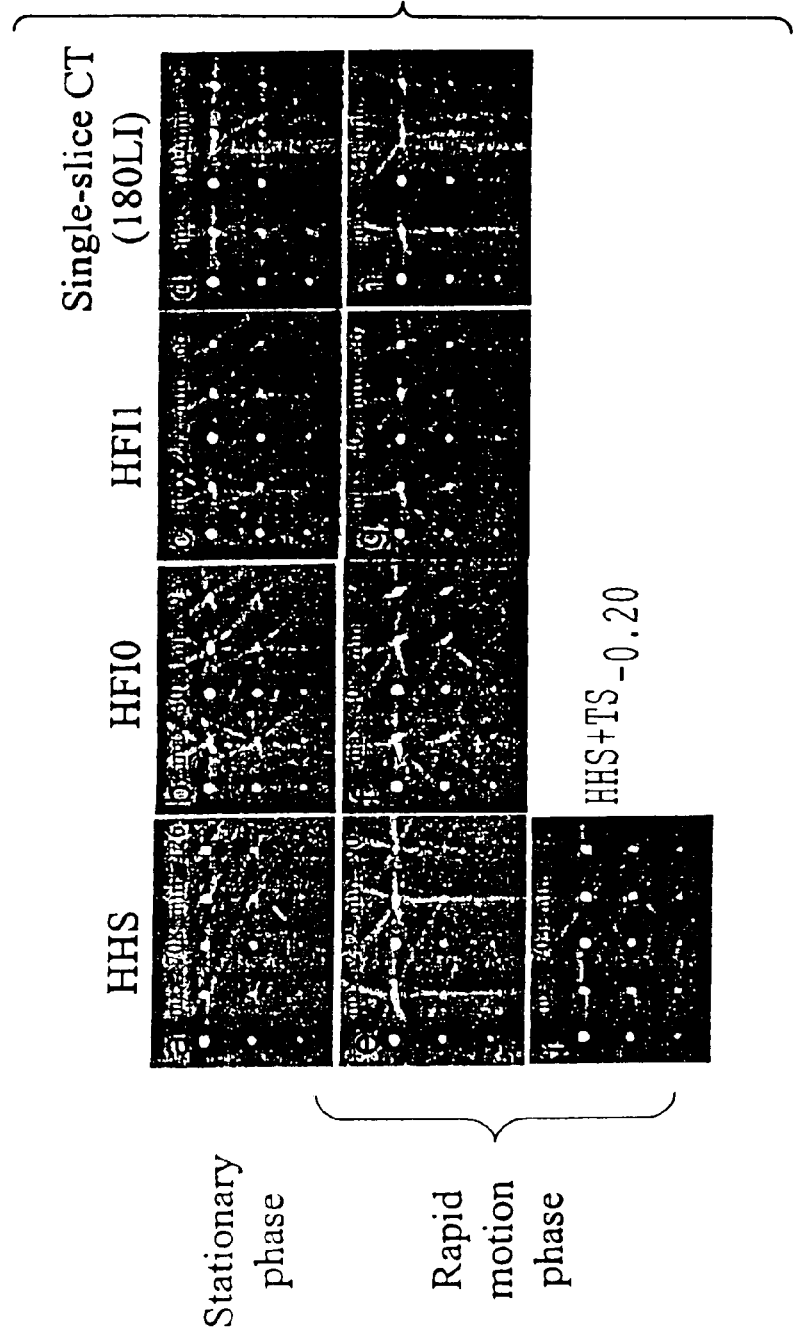
FIG. 22 is a diagram with sections (a)–(i) illustrating simulated phantom images at 90 cycles per second.

This tendency remained the same when the phantom objects move at 90 cycles per minute (FIG. 22). Note that TS could recover degraded CT values in the rapid motion phase of HHS almost to the level of stationary phase (FIGS. 8(a),(i)). Through this phantom study, $HFI_1$ kept constant level of image quality, although it was blurred and never better than HHS with TS technique. Again, HHS with TS shows the best imaging ability, with the image quality about the same as the stationary phase (compare (a) and (i)). The conditions for the 90 cycle data were the same as for the 60 cycle data.

Clinical Evaluation (1) Cardiac Imaging

Figure 23:
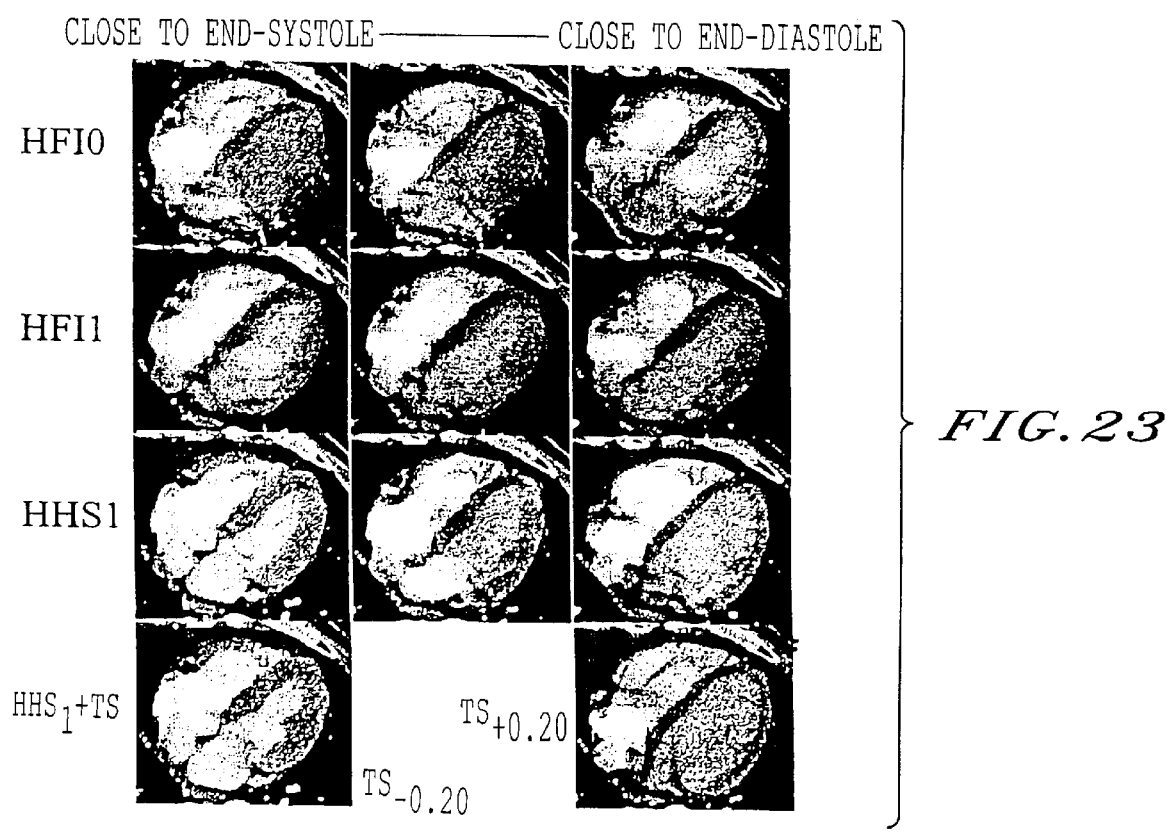
FIG. 23 are cardiac images taken using HFI, HHS, and HHS plus TS.

Referring to FIG. 23, images taken between end-systole and end-diastole at different slice positions (rows 1–3) and at the same positions (row 4) are shown. The heart rate for these images was 75/min. $HFI_1$ images show blurred outlines of the left ventricle and the interventricular septum (see first and third images of row 2), and could not image the variation in the thickness of the myocardium (see row 2). $HFI_0$ gave slightly sharper outlines of the myocardium but the tendency was the same (see row 1). HHS succeeded in imaging these features clearly, at both end-systole and end-diastole (see row 3, first and third images). Due to its better temporal resolution, HHS (rows 3 and 4) imaged the left ventricle and ventricular septum of the heart more sharply than did HFI (rows 1 and 2) for all images between end-systole and end-diastole. Between the systolic and the diastolic phases, cardiac wall motion becomes slower. Because of this, HHS could give images with sharp heart borders not only at end-diastole but also at end-systole, when most of the necessary data could be obtained within this period.

A combination of 0.5 sec. scanner rotation, multi-slice helical CT, and helical half scanning reconstruction were used, and enable sharp myocardial images at end-systole and end-diastole (first and third images of row 3). The window width and level were 400 and 40, respectively, and a standard body kernel (FC10) was used.

When the X-ray focus crosses the image plane between end-systole and end-diastole, a combination of HHS and TS allowed images to be obtained at the same slice position but at different times, close to end-systole and end-diastole, reducing the blurring seen in the heart wall (see row 4 and second image of row 3). Image noise with HHS was larger than that with HFI.

(2) Thoracic Imaging

Figure 24A:
FIGS. 24A–24D are thoracic images taken using HFI, HHS, and HHS plus TS.
Figure 24B:
Figure 24C:
Figure 24D:

FIGS. 24A–24D show the lung images obtained between end-diastole and end-systole. Due to the cardiac motion, $HFI_0$ showed strong artifacts (81 and 82 in FIG. 24A). The cardiac silhouette was delineated as double lines with $HFI_1$ (83 in FIG. 24B) and the margins of pulmonary vessels were blurred (84 in FIG. 24B). HHS without TS showed a motion artifact (85 in FIG. 24C) while HHS with TS technique gave sharp cardiac silhouettes and margins of pulmonary vessels, reducing the effect of cardiac motion (FIG. 24D). For these images the heart rate was 75/min and the standard thoracic kernel was used (FC50).

(3) Vascular Imaging

Figure 25A:
FIGS. 25A–25C are vascular images taken using HFI and HHS.
Figure 25B:
Figure 25C:

FIGS. 25A–25C are images of the thoracic aorta with contrast agent. The heart rate was 80/min. A standard body kernel was used (FC10) and the window width and level were 600 and 0, respectively. The images of the aorta show that HHS provided better image quality than HFI did, enabling sharp images of moving objects. Vessel pulsation caused the dissecting flap to be shown as double lines in HFI images indicating insufficient temporal resolution (FIGS. 25A and 25B). HHS images portrayed the anatomy accurately (FIG.

The method according to the invention, HHS has several advantages in cardiac imaging: (1) Non-gated HHS increases patient throughput; (2) either HHS with larger helical pitch or prospectively gated HHS allows reduced patient dose; (3) HHS enables retrospective cardiac imaging of the diastolic phase if EKG gating was not employed; and (4) HHS has the potential for better image quality in studies using contrast agents because HHS only uses consecutive half scanning data. For imaging relatively stationary phases, such as diastolic phase, HHS with TS is expected to have image quality comparable to that of the EKG gated reconstruction methods.

The method according to the invention can also obtain three dimensional (3D) images of the diastolic phase without EKG signals. A combination of scanning with small helical pitch (e.g., 1.5) in order to acquire necessary data (180°+ fan-angle) for each slice in the diastolic phase and adjusting the timing of TS for each slice manually, can reduce but cannot completely eliminate the stair step artifact in the 3D images. The causes of the artifact include the temporal gap between specific slices reconstructed by data obtained at different timings. Either of the following enhances the gap, hence, the artifact: respiration, patient motion, change in the contrast concentration, or other errors. Although it is not a principle issue but a practical one, the EKG signals, used for automatic timing adjustment in TS, can reduce the load of the task and are preferable.

Figure 26:
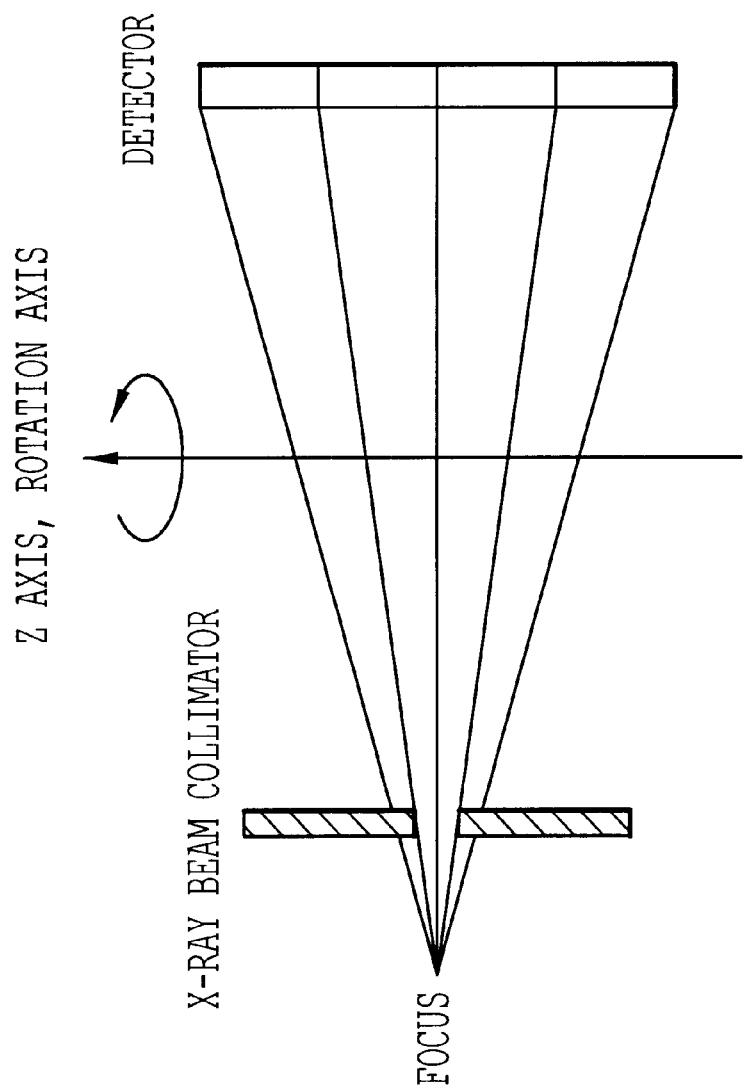
FIG. 26 is a diagram illustrating collimation to reduce patient dose.

As a further embodiment of the method according to the invention, it is also possible to reduce the patient dose. Some slice data sets are summed, average or weighted prior to helical interpolation (as described in the first part of the first embodiment). The slice positions are defined as the center of all slices. It can then be defined considering the weighting in the averaging process. For example, four-slice data may be averaged into two-slice data. In this case all of the data from the four slices are used in the helical interpolation which results in better image noise with some sacrifice of spatial resolution in the z direction. The patient dose may also be reduced by collimating the unnecessary x-ray beam for the outer slices before it reaches the patients, as shown in FIG. 26. A large helical pitch, TS, or longitudinal filtering requires data from outer slices. Otherwise, data from the outer slices are not used and represents unnecessary patient dose. Collimating the X-ray beam to exclude the outer slices thus making it a dual-slice CT, can reduce the patient dose while not affecting image quality or scan time. This may result in two-slice helical CT in some cases.

A further method of reducing a patient dose is to use gated triggering of the multi-slice helical scanning. The EKG signal is stored during helical scanning, as described above. The EKG signal is used as a trigger for the x-ray exposure. After a defined amount of scanning, x-ray exposure is automatically stopped. This procedure repeats during "fake multi-slice helical scanning (continuous tube rotation and continuous bed movement with no x-ray exposure). Limiting only the range to be scanned (the diastolic phase) the patient dose may be reduced.

Figure 27:
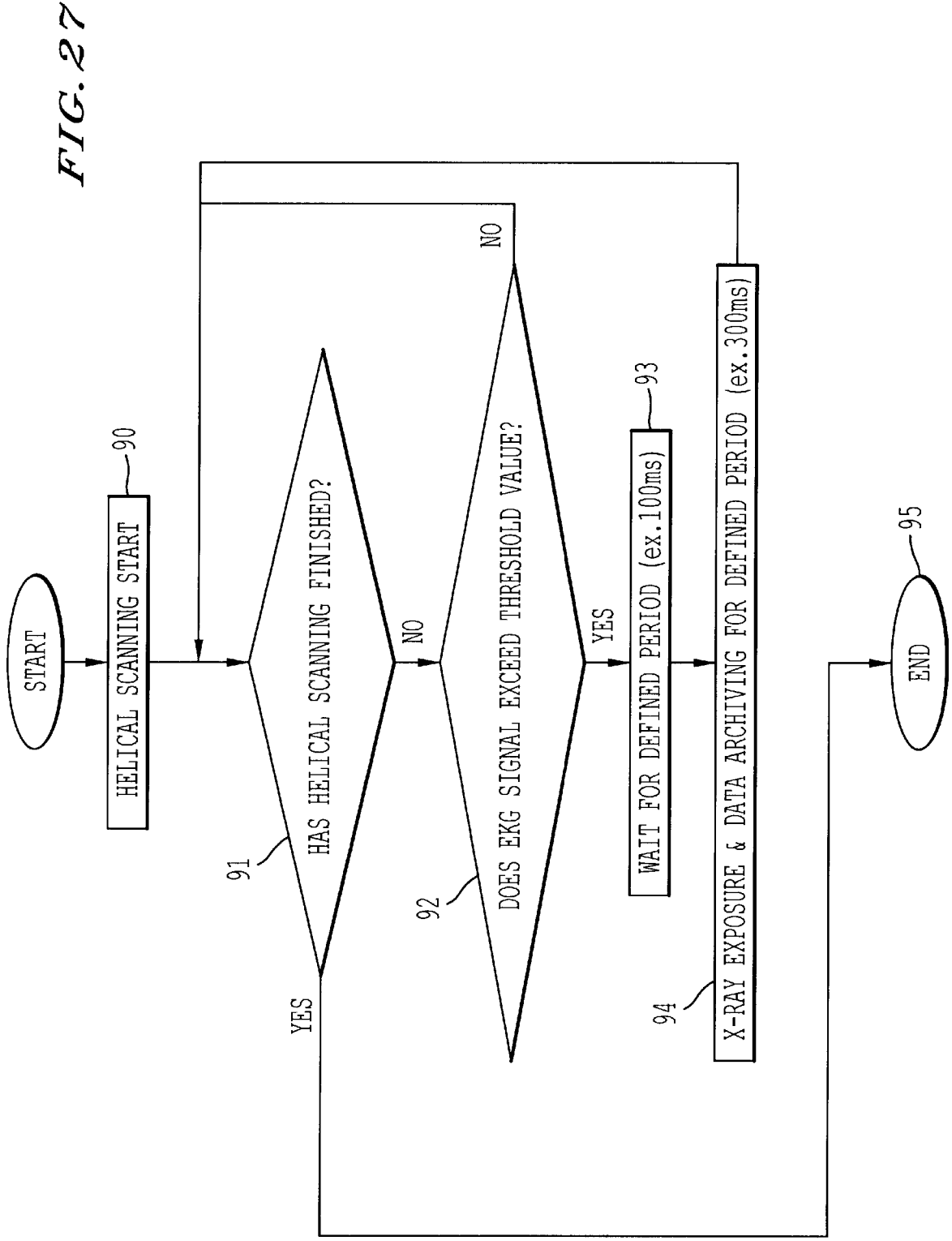
FIG. 27 is a flow chart illustrating EKG gating according to the present invention.

This method is illustrated in FIG. 27. In step 90, helical scanning is begun. A check is made in step 91 if the helical scanning has finished. If yes, the procedure ends at step 95. If no, it is determined whether the EKG signal exceeds the threshold value (step 92). If no, the procedure returns to step 91. If yes, the method proceeds to step 94 where the procedure waits for a defined period, such as 100 ms. The x-ray exposure and data archiving for the defined period is performed in step 94. This defined period may be, for example 300 ms. Step 94 then returns to step 92 to check whether helical scanning is finished.

In another embodiment of the method according to the invention, volume images are reconstructed at consecutive timings. Helical scanning is performed with a small helical pitch. The reconstruction technique used in this modification is one of those described above with relation to the timing shift technique. Selecting the time shift as a small increment in reconstructing all volume possible with helical scanning, some range of the volume may be reconstructed at a small timing pitch. This is illustrated in FIG. 28, where 100 represents a reconstructed slice using only interpolation (thinner line) and 101 represents a reconstructed slice using extrapolation (thicker line).

Obviously, numerous modifications and variations of the present invention are possible in light of the above teachings. For example, the step of the proposed method of helical interpolation, either nearest neighbor or non-linear interpolation can be applied in order to improve its spatial resolution or image quality. In the weighting step, any weighting can be applied for different purposes. It is therefore to be understood that within the scope of the appended claims, the invention may be practiced otherwise than as specifically described herein.

What is claimed and desired to be protected by Letters Patent is:

1. A computed tomography method, comprising:
   exposing a subject to X-rays while helically scanning;
   collecting data corresponding to an image of said subject;
   processing at least a portion of the collecting data obtained simultaneously;
   weighting the processed data by a weighting function;
   shifting the weighting function temporally; and
   reconstructing said image of said subject.

2. A method as recited in claim 1, comprising:
   obtaining processed data using only a portion of said data obtained simultaneously.

3. A method as recited in claim 1, comprising:
   obtaining sets of said data; and
   using weighted averaging to reduce a number of data sets.

4. A method as recited in claim 3, wherein processing said data comprises:
   using at least one of linear interpolation and extrapolation.

5. A method as recited in claim 3, wherein processing said data comprises:
   using at least one of non-linear interpolation and extrapolation.

6. A method as recited in claim 1, wherein processing said data comprises:
   using at least one of linear interpolation and extrapolation.

7. A method as recited in claim 1, wherein obtaining interpolated data comprises:
   using at least one of linear interpolation and extrapolation.

8. A method as recited in claim 1, comprising:
   obtaining complementary data corresponding to said processed data;
   obtaining a weighted summation of said processed data and said complementary data based upon said data collection timing; and
   reconstructing said image using said weighted summation.

9. A method as recited in claim 1, wherein:
   processing comprises filtering said data to obtain filtered data; and
   weighting comprises weighting said filtered data.

10. A method as recited in claim 1, wherein weighting comprises:
    using a weighting function having a value of zero except for a range of $\pi+2\gamma_m$ where $\gamma_m$ is a maximum channel angle.

11. A method as recited in claim 10, wherein said function comprises one of:

$$\beta_{new} = \beta - \beta_c + \frac{\pi + 2\gamma_m}{2}$$

and $$\beta_{new} = \beta - \beta_c + \pi.$$

12. A method as recited in claim 1, comprising:
    obtaining a signal from said subject; and
    shifting a timing for reconstructing said image using said signal.

13. A method as recited in claim 1, comprising:
    obtaining a signal from said subject; and
    controlling irradiation of said subject using said signal.

14. A method as recited in claim 1, wherein weighting comprises:
using a weighting function having a value of zero except for a range of $2\pi$.

15. A method as recited in claim 1, comprising:
collecting data corresponding to a cardiac image;
obtaining an EKG signal from said subject; and
shifting a timing for reconstructing said image using said signal.

16. A method as recited in claim 15, comprising:
obtaining data corresponding to substantially a diastolic phase of said subject.

17. A method as recited in claim 1, comprising:
simultaneously obtaining data for a plurality of rows of data; and
processing selected ones of said rows of data to yield said processed data.

18. A method as recited in claim 1, comprising:
simultaneously obtaining data for a plurality of rows of data;
selecting data from rows closest to portions of a slice being reconstructed for each portion; and
processing said data corresponding to each of said portions to yield said processed data.

19. A method as recited in claim 18, comprising:
selecting data from two of said rows closest to portions of a slice being reconstructed for each portion.

20. A method as recited in claim 1, wherein:
processing comprises interpolating said data to obtain interpolated data; and
weighting comprises weighting said interpolated data.

21. A method as recited in claim 1, wherein processing comprises:
at least one of interpolating and extrapolating said data to obtain said processed data.

22. A computed tomography system comprising:
a helical scanning unit for collecting helical data of a patient by a multi-slice helical scanning;
a weighting unit for weighting the helical data by a weighting function, including a mechanism configured to shift the weighting function along a temporal axis;
a reconstruction unit for reconstructing an image based on the weighted helical data.

23. A computed tomography system, comprising:
a radiation source;
a detector arranged to receive radiation from said source;
a processing circuit for processing data obtained using said detector;
a data collection timing weighting circuit connected to said processing circuit, for temporally shifting a weighting function; and
a reconstruction circuit connected to said weighting circuit.

24. A system as recited in claim 23, comprising;
a helical scanning device.

25. A system as recited in claim 23, wherein said processing circuit comprises at least one of a non-linear interpolation circuit and an extrapolation circuit.

26. A system as recited in claim 23, wherein said processing circuit comprises at least one of a linear interpolation circuit and an extrapolation circuit.

27. A system as recited in claim 23, wherein said processing circuit comprises a filter circuit.

28. A system as recited in claim 23, wherein said detector includes plural detector columns along a slice direction of a subject, the plural detector columns detecting the radiation simultaneously.

29. A system as recited in claim 23, wherein said weighting circuit comprises:
means for selectively temporally shifting a weighting function.

30. A system as recited in claim 23, comprising:
means for obtaining a signal from a subject irradiated by said source.

31. A system as recited in claim 30, comprising:
means for reducing a dose received by said subject using said signal.

32. A system as recited in claim 30, comprising:
means for selectively controlling irradiation by said source using said signal.

33. A system as recited in claim 23, comprising:
a collimator disposed to collimate radiation emitted by said source.

34. A system as recited in claim 23, wherein said weighting circuit comprises:
means for automatically temporally shifting a weighting function.

35. A system as recited in claim 23, further comprising:
a electrocardiograph for obtaining an electrocardiogram of a patient, and means for temporally shifting a weighting function according to the electrocardiogram.

36. A computed tomography system comprising:
an X-ray beam generating source;
an X-ray detector having detecting elements laid out in a plurality of rows along a slice direction of a subject, the detecting elements capable of detecting X-rays transmitted through the subject;
a moving unit for moving the subject along the slice direction;
a helical scanning unit for executing helical scanning by controlling said X-ray beam generating source, said X-ray detector, and said moving unit;
a data acquisition unit connected to said X-ray detector, for acquiring transmission data according to the transmitted X-rays detected by said X-ray detector;
a reconstruction unit for reconstructing images based on the transmission data; and
a weighting unit connected to said data acquisition unit, for weighting the transmission data by a weighting function, the weighting function being applied to the transmission data corresponding to at least a part of the rows and determined based on a data range required for reconstructing the image and shifted along a temporal axis.

37. A computed tomography system comprising:
an X-ray beam generating source;
an X-ray detector having detecting elements laid out in a plurality of rows along a slice direction of a subject, the detecting elements capable of detecting X-rays transmitted through the subject;
a moving unit for moving the subject along the slice direction;
a helical scanning unit for executing helical scanning by controlling said X-ray beam generating source, said X-ray detector, and said moving unit;
a data acquisition unit connected to said X-ray detector, for acquiring transmission data according to the transmitted X-rays detected by said X-ray detector;

a weighting unit connected to said data acquisition unit, for weighting the transmission data by a weighting function;

a weighting shifting unit connected to said weighting unit for shifting the weighting function along a temporal axis; and a tomographic images acquisition unit connected to said data acquisition unit, for obtaining tomographic images at a same slice position but at different times based on the weighted transmission data.

38. A computed tomography system comprising:

a helical scanning unit for collecting multi-slice helical data of a patient by multi-slice helical scanning;

an electrocardiograph for obtaining an electrocardiogram of the patient during the helical scanning;

a weighting unit connected to said helical scanning unit, for weighting the helical data by a weighting function;

a weighting shifting unit connected to said weighting unit for shifting the weighting function along a temporal axis; and a reconstruction unit for reconstructing images from the weighted helical data obtained at a specific cardiac phase according to the electrocardiogram.

39. A system as recited in claim 38, wherein said weighting unit selects a data range for reconstructing the image by shifting the weighting function.

40. A computed tomography system comprising:

a helical scanning unit for collecting multi-slice helical data of a patient by multi-slice helical scanning;

an electrocardiograph for obtaining an electrocardiogram of the patient during the helical scanning;

a reconstruction unit for reconstructing images from the helical data obtained at a specific cardiac phase according to the electrocardiogram; and a weighting unit for weighting the multi-slice helical data by a weighting function, including a mechanism configured to shift the weighting function along a temporal axis according to the electrocardiogram.

41. A system as recited in claim 40, wherein said weighting unit selects a data range for reconstructing the image by shifting the weighting function.

42. A computed tomography system comprising:

a helical scanning unit for collecting helical data of a patient by a helical scanning;

a weighting unit for weighting the helical data by a weighting function; and a tomographic images acquisition unit connected to said helical scanning unit, for obtaining images at a same position but at different times from the weighted helical data by shifting the weighting function along a temporal axis.

43. A system as recited in claim 42, wherein said helical scanning unit executes multi-helical scanning by a mechanism configured to have plural detector rows and plural detector columns along a slice direction of the patient, the plural detector columns detecting the radiation simultaneously.

* * * * *